US009002671B2

(12) United States Patent
Kan et al.

(10) Patent No.: US 9,002,671 B2
(45) Date of Patent: Apr. 7, 2015

(54) SYSTEMS AND METHODS FOR LATENCY AND MEASUREMENT UNCERTAINTY MANAGEMENT IN STIMULUS-RESPONSE TESTS

(75) Inventors: Kevin Gar Wah Kan, Philadelphia, PA (US); Christopher G. Mott, Seattle, WA (US); Daniel J. Mollicone, Philadelphia, PA (US)

(73) Assignee: Pulsar Informatics, Inc., Philadelphia, PA (US)

( * ) Notice: Subject to any disclaimer, the term of this patent is extended or adjusted under 35 U.S.C. 154(b) by 473 days.

(21) Appl. No.: 13/460,823

(22) Filed: Apr. 30, 2012

(65) Prior Publication Data

US 2012/0278022 A1  Nov. 1, 2012

Related U.S. Application Data

(60) Provisional application No. 61/481,039, filed on Apr. 29, 2011.

(51) Int. Cl.
*G06F 17/18* (2006.01)
*A61B 5/16* (2006.01)
*A61B 5/00* (2006.01)

(52) U.S. Cl.
CPC .............. *A61B 5/162* (2013.01); *A61B 5/7221* (2013.01)

(58) Field of Classification Search
CPC ...... A61B 5/162; A61B 5/7221; G06Q 30/02; G10L 25/78
USPC ...... 702/85, 80, 109, 112, 176, 179; 434/350; 704/211; 714/32; 340/575
See application file for complete search history.

(56) References Cited

U.S. PATENT DOCUMENTS 5,433,223 A    7/1995  Moore-Ede et al.
5,682,882 A   11/1997  Lieberman
(Continued)

OTHER PUBLICATIONS

Mathias Basner and David F. Dinges, "Maximizing Sensitivity of the Psychomotor Vigilance Test (PVT) to Sleep Loss," 34:5 SLEEP 581-591 (2011).

(Continued)

*Primary Examiner* — John H Le
(74) *Attorney, Agent, or Firm* — Damian M. Biondo, Esq.

(57) ABSTRACT

Disclosed are systems and methods for managing testing unit latency and measurement uncertainty in computer-based stimulus-response tests. An estimated latency $L_E$ and an associated measurement uncertainty are determined as characteristics of a particular testing unit. $L_E$ is used as offset for all measurements taken on the testing unit, and results treated subject to the characteristic measurement uncertainty when determining test-taker performance. Estimated actual response times $RT_E$ are processed subject to a confidence value determined from the uncertainty. Uncertainty propagation determines test metrics involving a plurality of estimated actual response times $RT_E$, where cumulative uncertainty is reported as a confidence rating in the metric. Overall test results (e.g., pass vs. fail) based on one or more metrics are also reported according to a confidence rating associated with the cumulative uncertainty propagated through the relevant metrics. Various calibration techniques are disclosed for determining the latency estimate $L_E$ and associated uncertainty values.

36 Claims, 14 Drawing Sheets

(56) References Cited

U.S. PATENT DOCUMENTS

| | | |
|---|---|---|
| 6,496,724 B1 | 12/2002 | Levendowski et al. |
| 6,511,424 B1 | 1/2003 | Moore-Ede et al. |
| 6,516,222 B2 | 2/2003 | Fukuda |
| 6,579,233 B2 | 6/2003 | Hursh |
| 6,712,615 B2 | 3/2004 | Martin |
| 6,782,372 B1 | 8/2004 | Cooper et al. |
| 7,076,697 B2 | 7/2006 | Lee |
| 7,130,761 B2 | 10/2006 | Hall et al. |
| 7,189,204 B2 | 3/2007 | Ni et al. |
| 7,461,321 B2 | 12/2008 | Lesartre |
| 7,509,253 B2 | 3/2009 | Luckett |
| 7,824,888 B2 | 11/2010 | Kondo |
| 7,860,561 B1 | 12/2010 | Modarres |
| 2003/0014464 A1 | 1/2003 | Deverill et al. |
| 2005/0004833 A1 | 1/2005 | McRae et al. |
| 2005/0004969 A1 | 1/2005 | McRae et al. |
| 2008/0231461 A1* | 9/2008 | Sanchez et al. ............... 340/575 |
| 2011/0054835 A1 | 3/2011 | Takamasu et al. |

OTHER PUBLICATIONS

Mathias Basner and Joshua Rubinstein, "Fitness for Duty: A 3-Minute Version of the Psychomotor Vigilance Test Predicts Fatigue-Related Declines in Luggage-Screening Performance," 53:10 J. Occ. & Envir. Med. 1146-1154 (Am. Col. Occ. & Envir. Med. 2011).

David F. Dinges and John W. Powell, "Microcomputer Analyses of Performance on a Portable, Simple, Visual RT Task During Sustained Operations," 17:6 Beh. Res. Meths. Instrs. & Comps. 652-655 (1985).

Jillian Dorrian, Naomi L. Rogers, and David F. Dinges, "Psychomotor Vigilance Performance: Neurocognitive Assay Sensitive to Sleep Loss," Sleep Deprivation: Clinical Issues, Pharmacology, and Sleep Loss Effects, 39-70 (Marcel Dekker, Inc. 2005).

\* cited by examiner

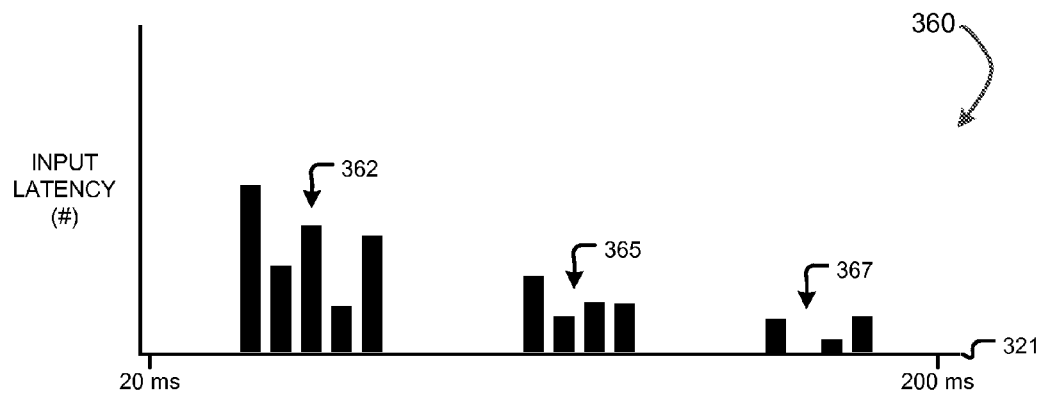
FIGURE 3D - I
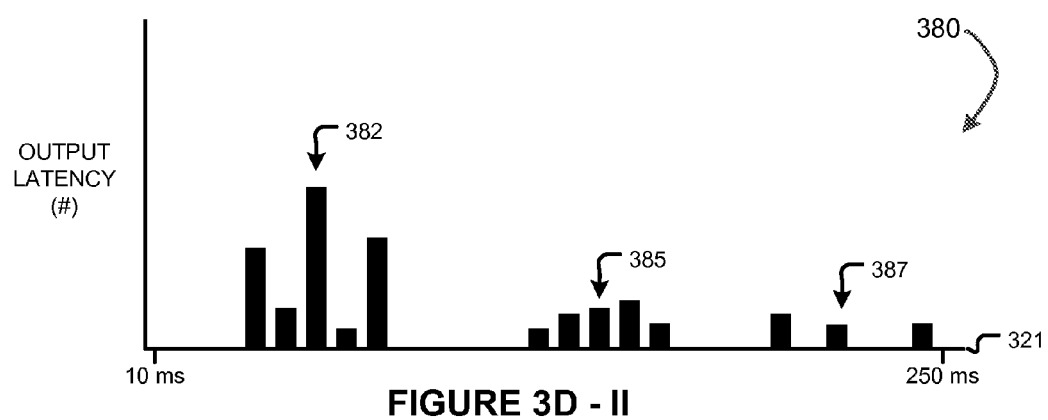
FIGURE 3D - II
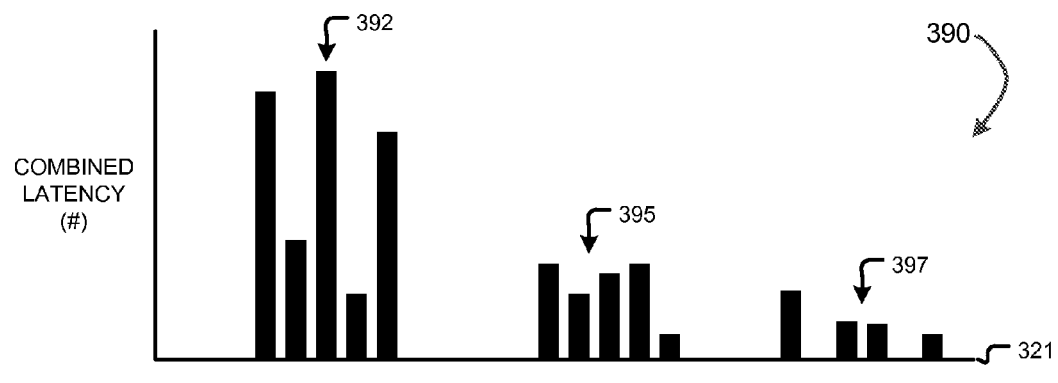
FIGURE 3D - III

$x_n$     The $n^{th}$ PVT measurement (in ms). $\{x_n\}$ represents the set of all PVT measurements in the test.
$u_n$     The uncertainty associated with the $n^{th}$ PVT measurement (in ms).
$N$     The total number of PVT measurements in the test. $\sum$ represents the sum over $n$, from $n=1$ to $n=N$.
$N_V, N_L, N_F, N_C, N_N, N_B$     The number of: Valid responses, Lapses, False starts, Coincident false starts, No responses, Buttons stuck
$M$     The metric value.
$U$     The total uncertainty associated with a metric value. In reporting a metric, it can be written as the metric value plus or minus the metric uncertainty, i.e., as $M \pm U$.

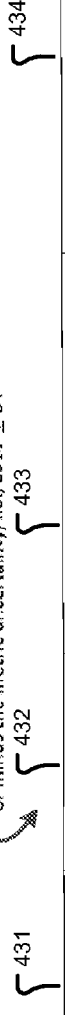

| Metric Name | Metric Description | Equation for the Metric | Equation for the Metric Uncertainty |
|---|---|---|---|
| MeanRT (ms) | Mean reaction time | $M = \frac{1}{N}\sum x_n$ | $U = \frac{1}{N}\sqrt{\sum (u_n)^2}$ |
| MeanRRT | Mean reciprocal of reaction times | $M = \frac{1}{N}\sum \frac{1}{x_n}$ | $U = \frac{1}{N}\sqrt{\sum \frac{(u_n)^2}{(x_n)^4}}$ |
| MeanFRT (ms) | Mean of fastest 10% reaction times | Same as MeanRT, except for the fastest 10% of $\{x_n\}$ | Same as MeanRT, except for the fastest 10% of $\{x_n\}$ |
| Lapses | Total lapse count (untransformed) | $M = N_L$ | See Note. |
| STDRT (ms) | Standard deviation of RT | Let $\bar{x}$ be the MeanRT defined above, then $M = \sqrt{\frac{1}{(N-1)}\sum (x_n - \bar{x})^2}$ | $U = \frac{1}{M(N-1)}\sqrt{\sum [(x_n - \bar{x})u_n]^2}$ |
| MeanSRT (ms) | Mean of slowest 10% reaction times | Same as MeanRT, except for the slowest 10% of $\{x_n\}$ | Same as MeanRT, except for the slowest 10% of $\{x_n\}$ |

FIGURE 4D

Note: The lapse metric counts the number of RTs greater than $L_{Threshold}$: $N_L = \sum X_n > L_{Threshold}$. The uncertainty varies based on the uncertainty distribution. For an uniform distribution the probability that a given response should be counted as a lapse is $p_n$ is the integral $\int U(t;x_n-\sqrt{3}u_n, x_n+\sqrt{3}u_n)dt$ of the uniform distribution with the limits of integration from $L_{Threshold}$ to infinity. For an uncertainty distribution that is Gaussian then $p_n = 1 - \Phi(L_{Threshold} | \mu=x_n, \sigma=u_n)$, where $\Phi$ is the Gaussian cdf. The expected number of lapses is $\sum p_n$ and the overall metric uncertainty standard deviation is $\sqrt{\sum p_n(1-p_n)}$.

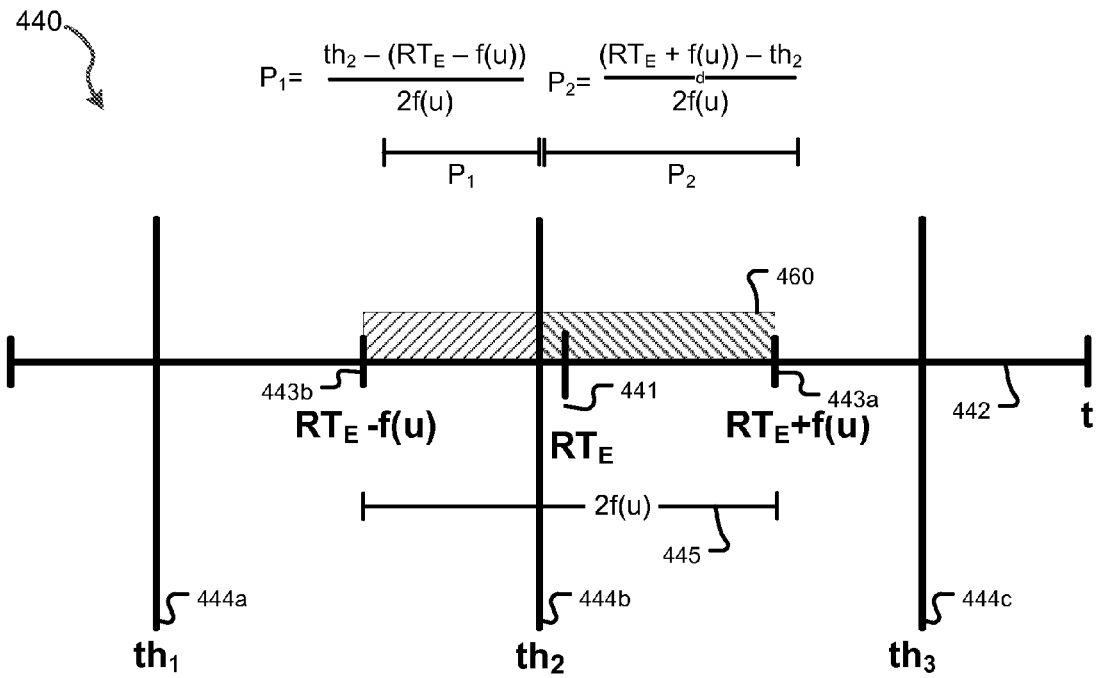
FIGURE 4E - I
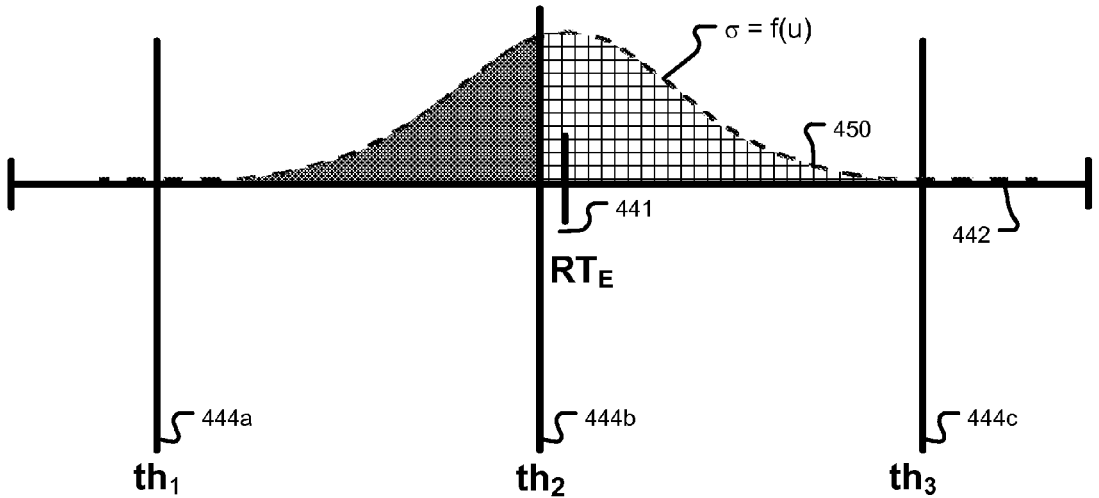
FIGURE 4E - II

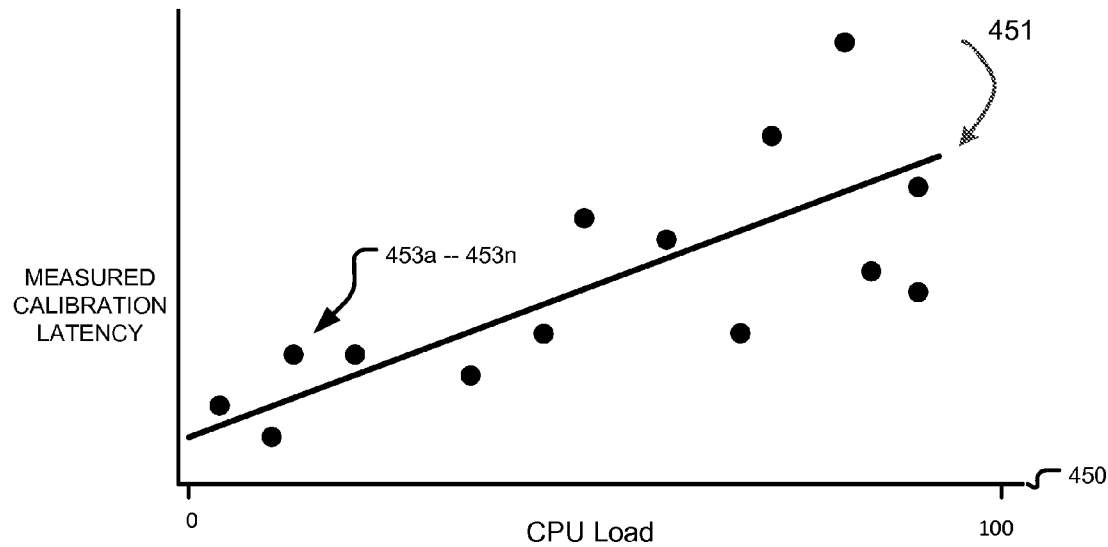
FIGURE 4F - I
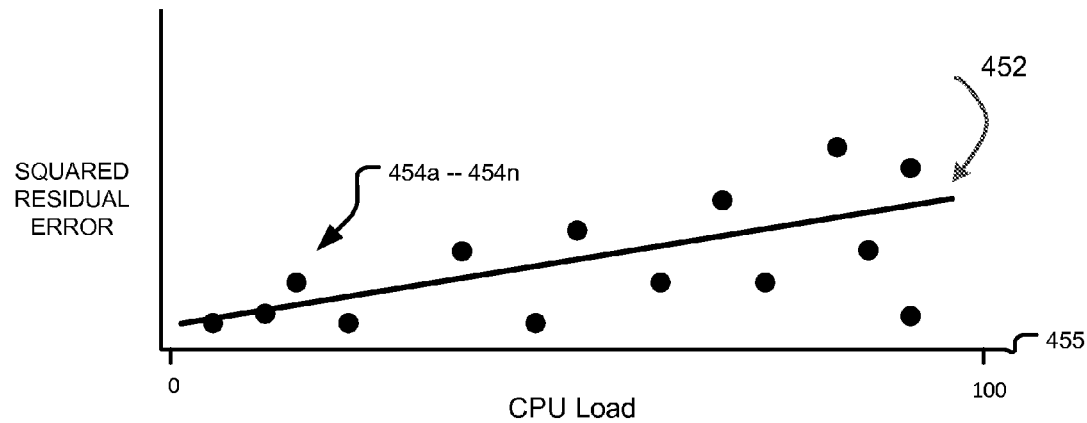
FIGURE 4F - II

SYSTEMS AND METHODS FOR LATENCY AND MEASUREMENT UNCERTAINTY MANAGEMENT IN STIMULUS-RESPONSE TESTS

RELATED APPLICATIONS

This application claims benefit of the priority of U.S. Provisional Patent Application No. 61/481,039, filed Apr. 29, 2011.

TECHNICAL FIELD

The presently disclosed systems and methods relate generally to computer-based stimulus-response tests. Particular embodiments provide systems and methods for the management of latency and measurement uncertainty in the administration of computer-based stimulus-response tests.

BACKGROUND

Stimulus-response tests (specifically, reaction-time tests) are used in a variety of contexts to assess aspects of an individual's neurobehavioral state. The response-time measurements are often analyzed down to millisecond-level discrimination. Timing accuracy and precision at the millisecond level, however, is not consistently achieved by most general-purpose, commercially available, computer-based testing systems. Latencies associated with computer-based testing systems typically limit the ability to obtain such accuracy. These latencies may arise by virtue of the hardware elements involved in the testing system (e.g., I/O controller delays, I/O device polling frequencies, signal travel time between hardware components, and/or the like) and/or extraneous software processes that are not a part of the stimulus-response test being run on the test system (e.g., operating system overhead, applications, viruses and malware, and/or the like). It is desirable to have methods for determining the timing latencies and uncertainties in a computer-based testing system, and reflecting these factors into the performance indicators related to the test taker.

SUMMARY

One aspect of the invention provides a processor-based method for scoring a stimulus-response test for a test taker with a confidence value based on response-time measurement uncertainty, the method comprising: providing a testing unit, the testing unit comprising: a processor, an input device accessible to a test taker, an output device accessible to the test taker, an output data path connecting the processor to the output device, and an input data path connecting the input device to the processor; administering a stimulus-response test to the test taker, administering the stimulus-response test comprising conducting a plurality of stimulus-response rounds, each of the plurality of stimulus-response rounds comprising: sending a stimulus signal from the processor to the output device via the output data path, the stimulus signal sent from the processor at a first time $t_1$, the stimulus signal causing the output unit to output a stimulus and prompting the test taker to respond to the stimulus at the input device; receiving a response signal from the input device at the processor via the input data path, the response signal received at the processor at a second time $t_2$; determining a round-trip signal time $T_{RTS}$ comprising a time interval between the first and second times; determining an estimated actual response time $RT_E$ to be a difference between the round trip signal time $T_{RTS}$ and a latency estimate $L_E$, the latency estimate $L_E$ representing an estimate of a combination of: an output latency time between the first time $t_1$ and a time that the stimulus is output from the output device; and an input latency time between a time that the test taker responds to the stimulus at the input device and the second time $t_2$; determining one or more uncertainty values representing uncertainty associated with the plurality of estimated actual response times $RT_E$; determining a performance indicators for the test taker, the performance indicator based on the plurality of estimated actual response times $RT_E$; and determining a confidence value, the confidence value based on the one or more uncertainty values and representative of a confidence in the performance indicator.

Aspects of the invention may be provided as a computer program product embodied in non-transitory media and comprising computer-readable instructions which when executed by a suitable computer may cause the computer to perform any of the methods disclosed herein. Specifically, another particular aspect of the invention provides a computer program product embodied in non-transitory media and comprising computer-readable instructions which when executed by a suitable computer may cause the computer to perform a processor-based method for scoring a stimulus-response test for a test taker with a confidence value based on response-time measurement uncertainty, the method comprising: providing a testing unit, the testing unit comprising: a processor, an input device accessible to a test taker, an output device accessible to the test taker, an output data path connecting the processor to the output device, and an input data path connecting the input device to the processor; administering a stimulus-response test to the test taker, administering the stimulus-response test comprising conducting a plurality of stimulus-response rounds, each of the plurality of stimulus-response rounds comprising: sending a stimulus signal from the processor to the output device via the output data path, the stimulus signal sent from the processor at a first time $t_1$, the stimulus signal causing the output unit to output a stimulus and prompting the test taker to respond to the stimulus at the input device; receiving a response signal from the input device at the processor via the input data path, the response signal received at the processor at a second time $t_2$; determining a round-trip signal time $T_{RTS}$ comprising a time interval between the first and second times; determining an estimated actual response time $RT_E$ to be a difference between the round trip signal time $T_{RTS}$ and a latency estimate $L_E$, the latency estimate $L_E$ representing an estimate of a combination of: an output latency time between the first time $t_1$ and a time that the stimulus is output from the output device; and an input latency time between a time that the test taker responds to the stimulus at the input device and the second time $t_2$; determining one or more uncertainty values representing uncertainty associated with the plurality of estimated actual response times $RT_E$; determining a performance indicator for the test taker, the performance indicator based on the plurality of estimated actual response times $RT_E$; and determining a confidence value, the confidence value based on the one or more uncertainty values and representative of a confidence in the performance indicator.

Aspects of the invention may be provided as a system comprising a processor capable of executing instructions which when executed may cause the system to perform any of the methods disclosed herein. Specifically, another particular aspect of the invention provides a system for scoring a stimulus-response test for a test taker with a continuous value based on response-time measurement uncertainty, the system comprising: a processor, an input device, an output device, an out data path connecting the processor to the output device, and an input data path connecting the input device to the processor; wherein the processor is configured to: administer the stimulus-response test comprising conducting a plurality of stimulus-response rounds, each of the plurality of stimulus-response rounds comprising: sending a stimulus signal from the processor to the output device via the output data path, the stimulus signal sent from the processor at a first time $t_1$, the stimulus signal causing the output unit to output a stimulus and prompting the test taker to respond to the stimulus at the input device; receiving a response signal from the input device at the processor via the input data path, the response signal received at the processor at a second time $t_2$; determining a round-trip signal time $T_{RTS}$ comprising a time interval between the first and second times; determining an estimated actual response time $RT_E$ to be a difference between the round trip signal time $T_{RTS}$ and a latency estimate $L_E$, the latency estimate $L_E$ representing an estimate of a combination of: an output latency time between the first time $t_1$ and a time that the stimulus is output from the output device; and an input latency time between a time that the test taker responds to the stimulus at the input device and the second time $t_2$; determine one or more uncertainty values representing uncertainty associated with the plurality of estimated actual response times $RT_E$; determine a performance indicator for the test taker, the performance indicator based on the plurality of estimated actual response times $RT_E$; and determining a confidence value, the confidence value based on the one or more uncertainty values and representative of a confidence in the performance indicator.

BRIEF DESCRIPTION OF THE DRAWINGS

FIG. 3D is a set of example histograms representative of latency measurements associated with stimulus-response rounds into input latency times, output latency times, and combined latency times;

FIG. 4D provides a table illustrating a sample set of PVT test metrics and their corresponding description, equation for the metric, and equation for the metric uncertainty, in accordance with a particular embodiment;

FIG. 4E provides a chart illustrating how confidence values associated with primary and secondary response time classifications are determined, in accordance with a particular embodiment; and The multiple views of FIG. 4F illustrate the mathematical techniques for determining a latency estimate $L_E$ and associated uncertainty values from a set of calibration latency data using linear regression methods, in accordance with a particular embodiment.

DETAILED DESCRIPTION

Figure 1A:
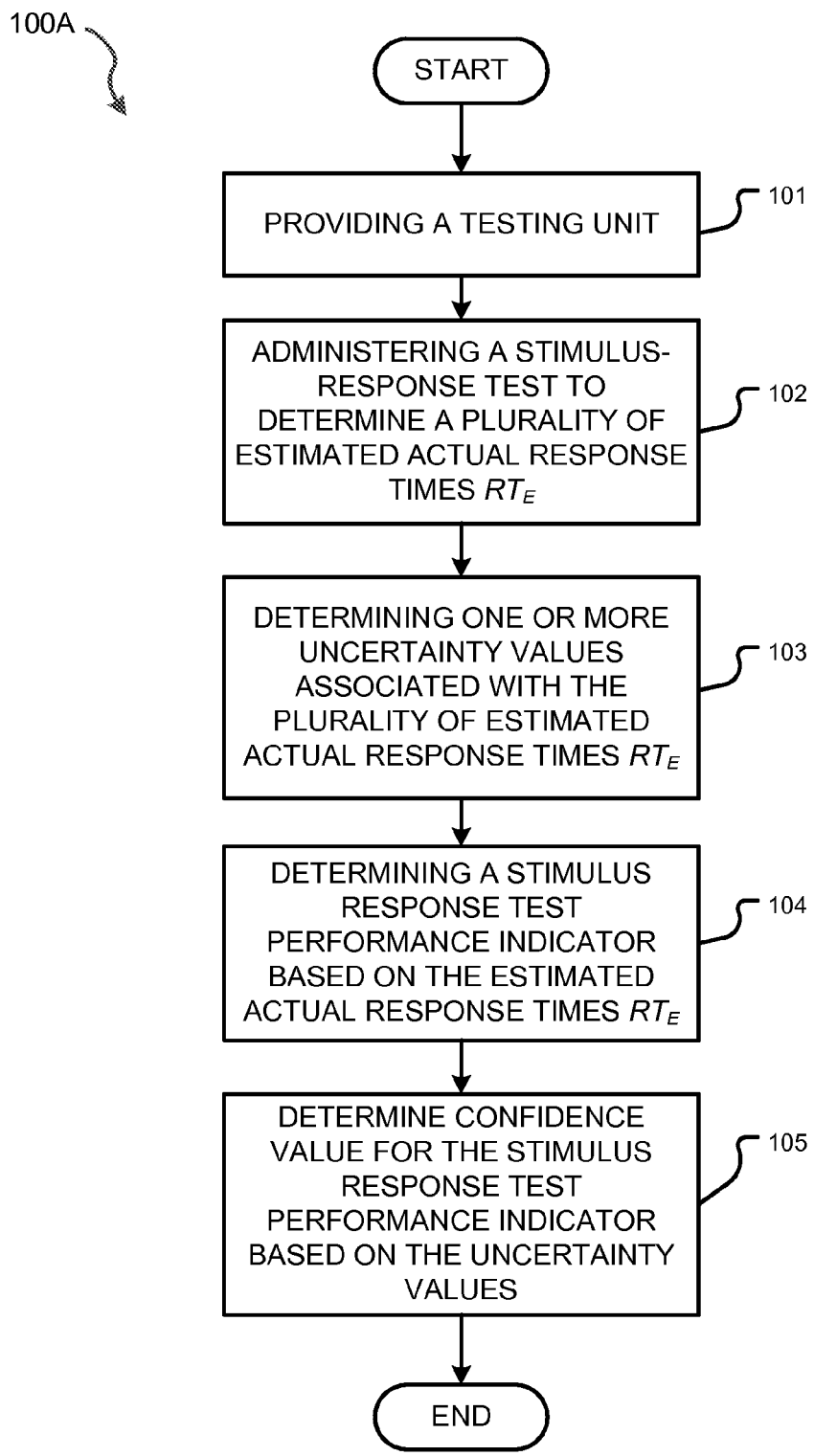
FIG. 1A contains a flow chart illustrating a method for providing a stimulus-response test involving management of latency and measurement uncertainty, in accordance with a particular embodiment.

Throughout the following description, specific details are set forth in order to provide a more thorough understanding of the invention. However, the invention may be practiced without these particulars. In other instances, well-known elements have not been shown or described in detail to avoid unnecessarily obscuring the invention. Accordingly, the specification and drawings are to be regarded in an illustrative capacity, rather than a restrictive sense.

Stimulus-response tests may be used to measure the reaction time of a testing subject in order to quantify one or more of the subject's neurobehavioral states, including but not limited to fatigue state (or its inverse, alertness state). Such tests involve the presentation of one or more stimulus events (or stimulus triggers, or simply "stimulus") to the subject and the measurement or recording of the characteristics of the stimulus and the subject's subsequent response. Non-limiting examples of stimulus-response tests include: the psychomotor vigilance test (PVT), digit symbol substitution task (DSST) tests, Stroop tests and the like. Individuals who take or are otherwise subjected to stimulus-response tests may be referred to herein interchangeably as "test takers," "testing subjects," and/or "subjects."

Reaction-time tests represent a particular example of a stimulus-response test in which the time delay between the stimulus trigger and the subject's response is of particular interest. Reaction-time tests represent a common assessment technique for evaluating human cognitive and neurobehavioral performance, including (but not limited to) fatigue and/or alertness. Generally, reaction-time tests involve: presenting a stimulus event to the subject, measuring or recording a time at which the stimulus event is presented, and measuring or recording a time at which the subject responds to the stimulus. Oftentimes, several rounds of stimuli are presented and responses received in a series of separately identifiable stimulus-response rounds. See, e.g., U.S. patent application Ser. No. 12/776,142, entitled Systems and Methods for Evaluating Neurobehavioral Performance from Reaction Time Tests, K. Kan, C. Mott et al., inventors, (USPTO Pub. No. 2010/0311023) the entirety of which is hereby incorporated by reference, for a method to process reaction time data using weighting functions.

As a non-limiting example, one use of stimulus-response tests, generally, and reaction-time tests, specifically, is to estimate the subject's level of fatigue. The fatigue level of a subject may be used to gauge that subject's ability to perform a task safely that may be susceptible to fatigue related errors and accidents (e.g. piloting a jet fighter).

Stimulus-response tests (including reaction-time tests) may be administered on a wide variety of hardware and software platforms. For example, stimulus-response tests may be administered on personal computers, which comprise relatively common stimulus output devices (e.g. monitors, displays, LED arrays, speakers and/or the like) and relatively common response input devices (e.g. keyboards, computer mice, joysticks, buttons and/or the like). As another example, stimulus-response tests can be administered by dedicated hardware devices with particular stimulus output devices and corresponding response input devices.

When comparing the results of stimulus-response tests administered on different hardware and/or software systems, one additional issue to address—particularly when the timing of a response relative to a stimulus event is of interest—is the latency between various components of the hardware and/or software systems. By way of non-limiting example, there may be latency associated with a computer implementing a stimulus-response test, latency of a response input device, latency of a stimulus output device, latency of the interfaces between the components of a system implementing a stimulus-response test, and/or the like. Such latencies may be different for different hardware and/or software systems. Furthermore, the latency of any given component may not be fixed or even well-known initially. See, e.g., U.S. patent application Ser. No. 12/777,107, (Publication No. 2010/0312508) Methods and Systems for Calibrating Stimulus-Response Testing Systems, the entirety of which is hereby incorporated by reference, for systems and methods to measure and to address issues of latency in testing systems.

Figure 2A:
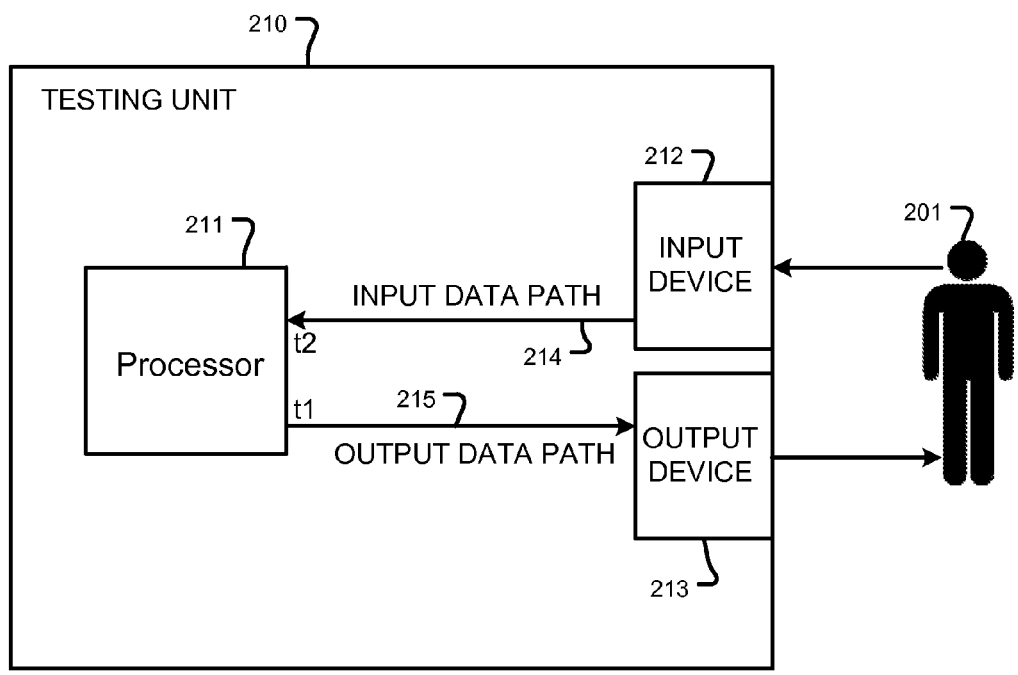
FIG. 2A is a schematic block diagram depicting the basic components of a stimulus-response testing unit, in accordance with a particular embodiment.

By way of introduction, FIG. 2A provides a component diagram of a testing unit 210 as provided to a test taker 201 in accordance with step 101 of method 100A (FIG. 1A). Testing unit 210 comprises a processor 211, an input device 212, and an output device 213. An output data path 215 connects processor 211 to output device 213, and an input data path connects input device 212 to processor 211. Also illustrated is test taker 201, who is capable of interacting with output device 213 and input device 212. Processor 211 may comprise any one or more suitable devices or components for the execution of computer instructions, such as a programmable central processing unit within a computing device, a multi-core processor, an embedded controller microchip, and/or the like. Output device 213 may comprise any suitable device for communicating a stimulus to the test taker 210, such as a monitor, video screen, loudspeaker, haptic feedback device, LED or LED panel, and/or the like. Input device 212 may comprise any suitable device for receiving a response from test taker 210, such as a keyboard, mouse, joystick, game controller, push button, touch screen, microphone, camera, video camera, and/or the like. Testing unit 210 may comprise any suitable device for executing a stimulus-response test, such as a personal computer, a mobile device, a client-server network, a dedicated stimulus-response control box, a wrist-worn device, and/or the like.

FIG. 1A provides a flowchart depicting a method 100A for providing a stimulus-response test involving management of latency and measurement uncertainty in accordance with a particular embodiment. Method 100A begins with step 101 in which a stimulus-response testing unit 210 (FIG. 2A) is provided to a test taker 201 (FIG. 2A). A stimulus-response test is then administered, in step 102, to a test taker 201 to determine a plurality of estimated actual response times, denoted $RT_E$. Estimated actual response times $RT_E$ may each comprise a measured response time adjusted by a corresponding latency estimate $L_E$. Latency estimate $L_E$ may be associated with testing unit 210 (FIG. 2A) and determined independently, by way of non-limiting example, through calibration and measurement. (See FIG. 1C for details of an exemplary but non-limiting calibration technique, method 100C.) One or more uncertainty values associated with the plurality of estimated actual response times $RT_E$ are then determined in step 103. The one or more uncertainty values associated with the plurality of estimated actual response times $RT_E$ may reflect the uncertainty or variability associated with the latency estimate $L_E$ associated with testing unit 210 and/or the measurement uncertainty associated with determining estimated actual response times $RT_E$ in accordance with step 102. In those embodiments in which the latency estimate LE is determined through calibration method 100C, the latency estimate may comprise the mean, median, or average value of the set of measured or inferred latency values during calibration. Similarly step-103 uncertainty values may comprise a statistical measure representative of the spread or width (e.g., variance, standard deviation, and/or the like) of the distribution of measured or inferred latency values during calibration method 100C. Both the latency estimate $L_E$ and the step-103 uncertainty values may be characteristics of a particular testing unit 210, or may be ascertained from a look-up table or other database of available testing units 210 comprising known hardware and/or software components.

A stimulus-response test performance indicator is then determined in step 104 in accordance with one or more test metrics, which are discussed in connection with FIGS. 4A through 4E, below. Step 105 involves determining a confidence value that represents the confidence with which the test performance indicator may be reported. The step-105 confidence value may be based at least in part on the step-103 measurement uncertainty values.

Figure 1B:
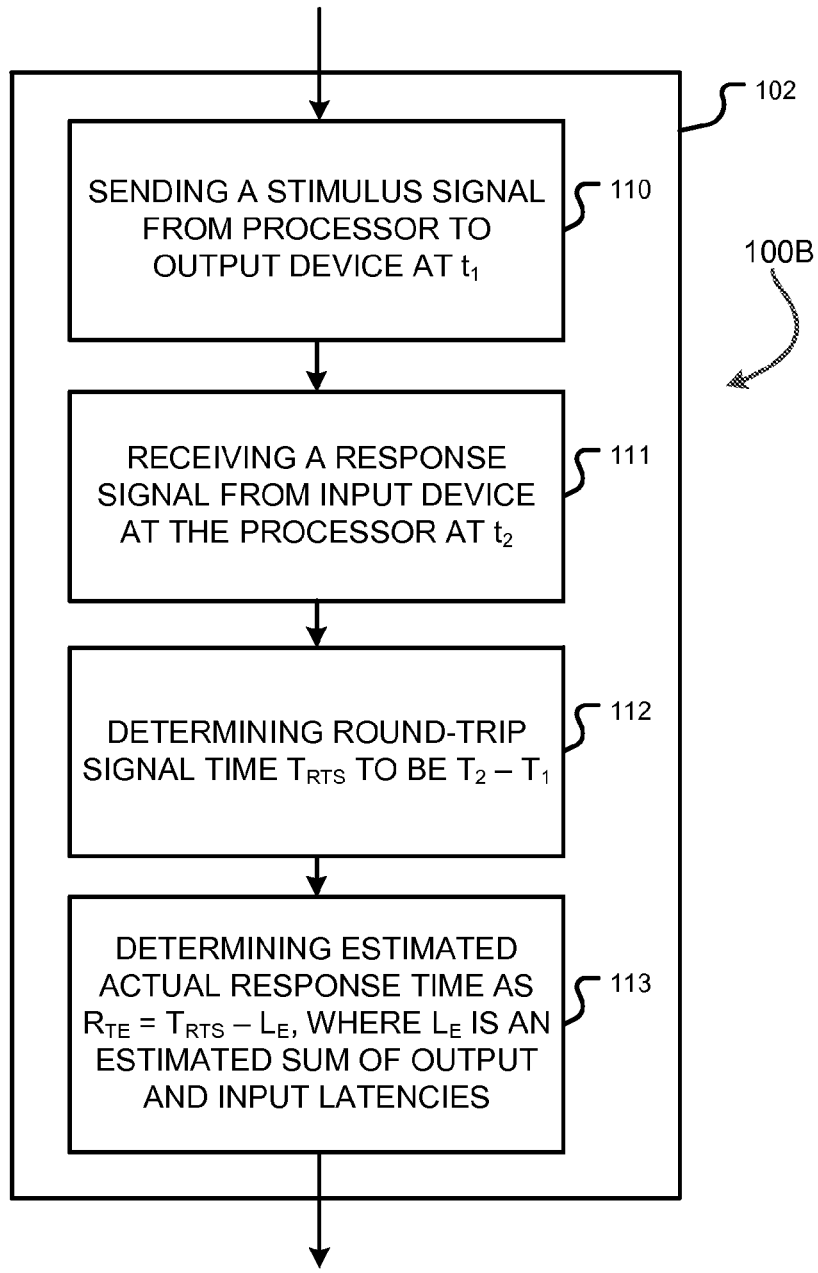
FIG. 1B contains a flow chart illustrating a method for determining estimated actual response times $RT_E$ using a latency estimate $L_E$ in accordance with a particular embodiment.

FIG. 1B provides a flowchart illustrating method 100B, which provides additional process details for step 102 of method 100A (i.e., determining estimated actual response times $RT_E$), in accordance with a particular embodiment. Method 100B commences with step 110 in which a stimulus signal is sent from processor 211 to an output device 213 at a specific time, denoted $t_1$. Processor 211 may measure or otherwise record time $t_1$. A response signal is then received at the processor 211 at a subsequent time $t_2$, in step 111. Processor 211 may measure or otherwise record time $t_2$. A round-trip signal time $T_{RTS}$ is then determined in step 112 as the difference between the second and first times—i.e., $T_{RTS}=t_2-t_1$. A latency estimate $L_E$ is then subtracted from the round-trip signal time $T_{RTS}$ in step 113 to determine an estimated actual response time—i.e., $RT_E=T_{RTS}-L_E$. In particular embodiments latency estimate $L_E$ represents a statistical measure (e.g., the mean, expected value, or average etc.), which is representative of various variable and non-deterministic latencies caused by the testing unit 210. The latency estimate $L_E$ may be determined over a large number of stimulus-response calibration iterations as explained in further detail in connection with FIGS. 1C, 1D, 3C, and 3D. In those embodiments where latency estimate $L_E$ comprises the expected value of a set of all measured or inferred latencies determined over a large number of calibration iterations, the step-103 determined uncertainty values may comprise a statistical measure representative of the spread (e.g., variance, standard deviation, etc.) of the set.

Figure 1C:
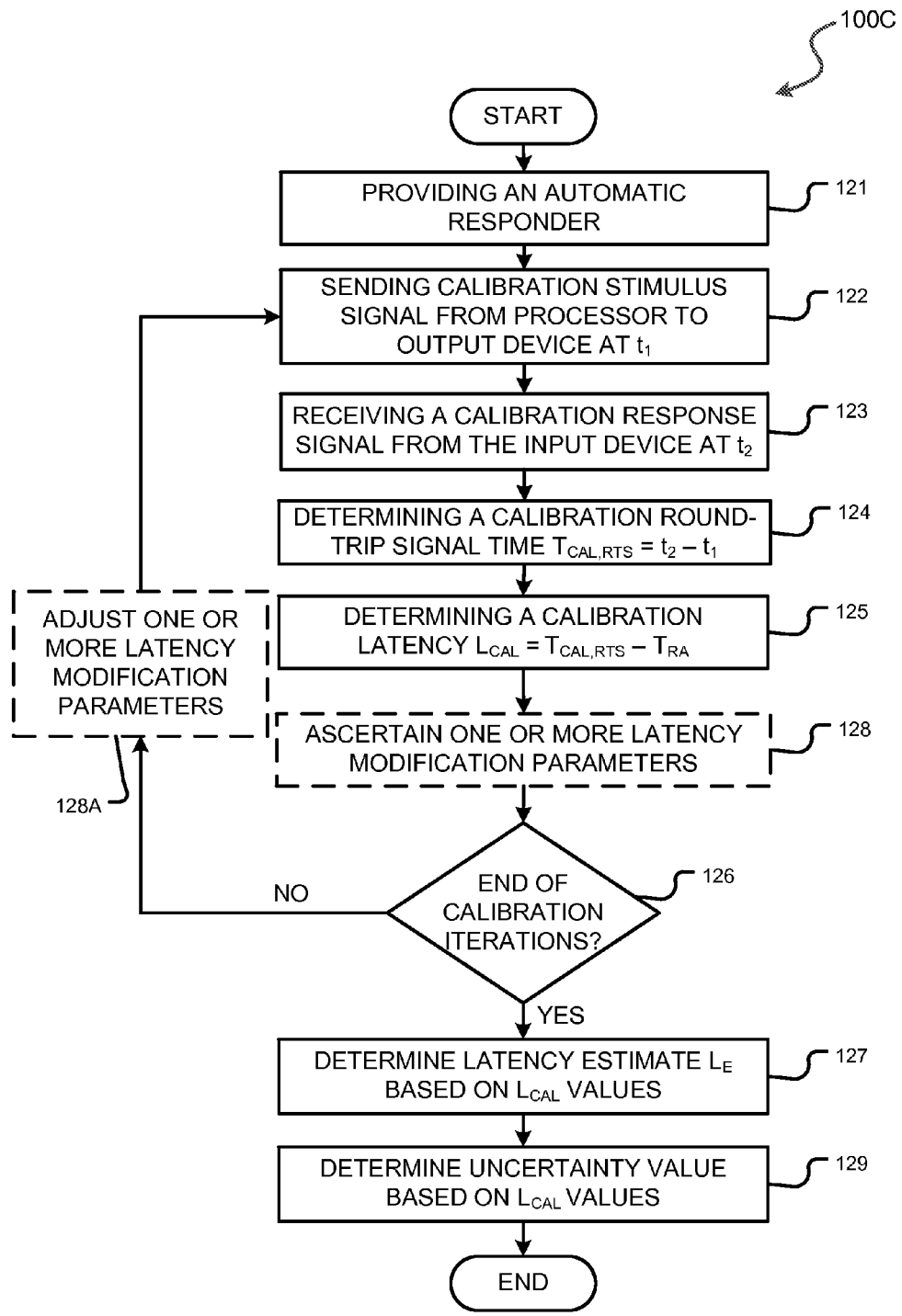
FIG. 1C contains a flow chart illustrating a method to determine a latency estimate $L_E$ for a testing unit using a calibration procedure, in accordance with a particular embodiment.
Figure 2B:
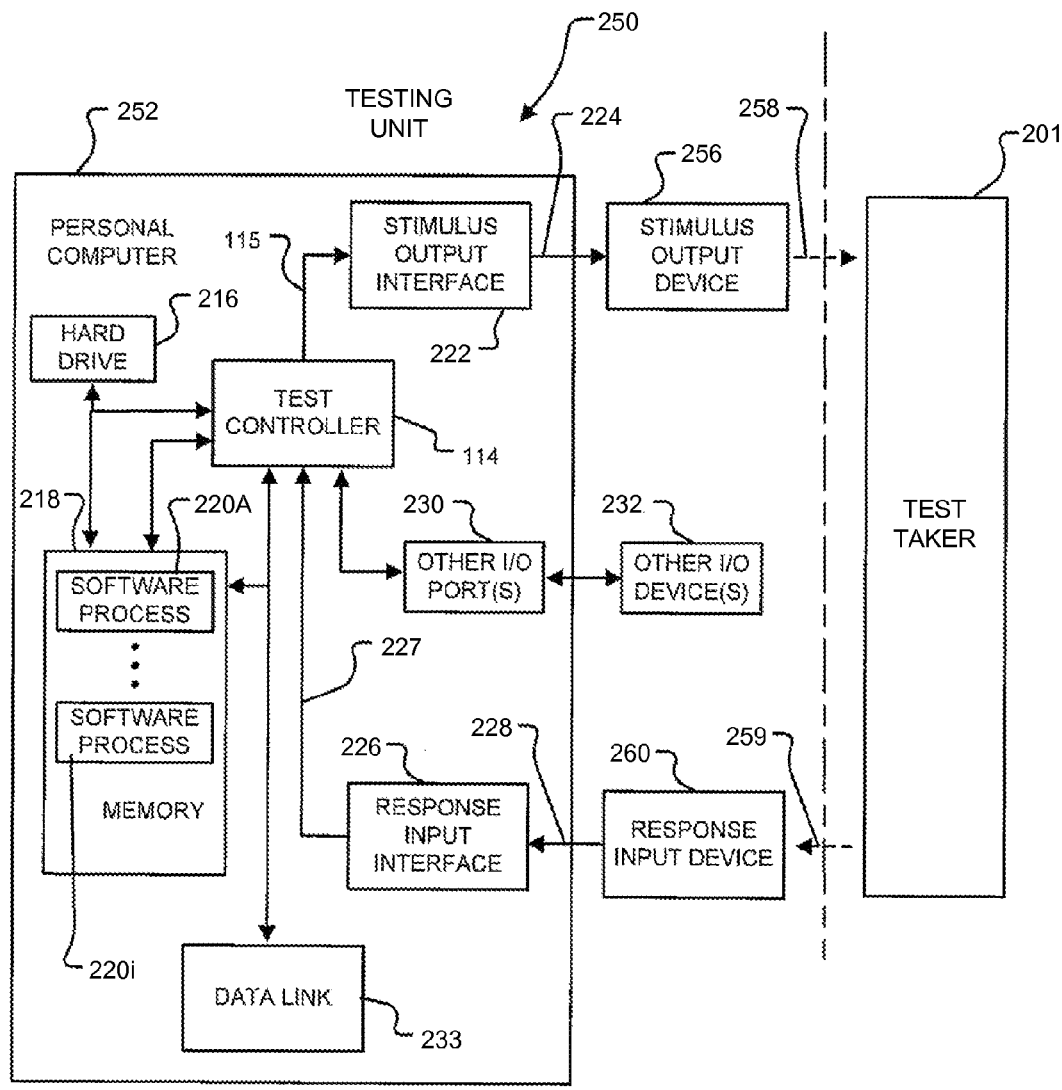
FIG. 2B is a block diagram depicting a stimulus-response testing unit in accordance with a particular embodiment.

FIG. 1C provides a flowchart illustrating a method 100C for calibrating a testing unit 201, 250 (FIGS. 2A and 2B, respectively) to determine values for the latency estimate $L_E$ and corresponding uncertainty associated with the testing unit 201, 250 according to a particular embodiment. Method 100C commences in step 121, wherein an automatic responder with a known automatic-responder response time $T_{RA}$ is provided. Such an automatic responder may effectively take the place of test taker 201 (FIG. 2A, 2B) and may respond to stimuli in the place of test taker 201. The automatic responder can be any device, system, or component that is capable of receiving the stimulus 258 (FIG. 2B) from testing unit 201, 250 and, within a fixed, known time $T_{RA}$, responding with an input response 259 (FIG. 2B). Without limitation, U.S. Patent Application Publication No. 2010/0312508, entitled Methods and Systems for Calibrating Stimulus-Response Testing Systems, submitted by C. Mott and D. Mollicone, the entirety of which has been incorporated by reference herein, contains an exemplary but non-limiting embodiment of an automatic responder capable of use in step 121. Step 122 involves sending a stimulus signal at time $t_i$ from processor 211 or test controller 114 to an output device 213, 256 along output data path 215. The time $t_1$ may be measured or otherwise recorded.

The automatic responder then detects the stimulus from output device 213, 256, and responds to the stimulus by activating input device 212, 260. Response signal 227 is then detected at processor 211 or test controller 114 at time $t_2$ in step 123. The time $t_1$ may be measured or otherwise recorded. Step 124 proceeds by determining a calibration round-trip signal time $T_{CAL,RTS}$ to be a difference between $t_2$ and $t_1$ (i.e., $T_{CAL,RTS}=t_2-t_1$). Then step 125 determines a calibration latency $L_{CAL}$ as the difference between the calibration round-trip signal time $T_{CAL,RTS}$ and the automatic-responder response time $T_{RA}$ (i.e., $L_{CAL}=T_{CAL,RTS}-T_{RA}$).

Optionally, one or more latency modification parameters of testing unit 201, 250 may be ascertained (e.g., measured or otherwise obtained) in each iteration of step 128. Latency modification parameters may include (but are not limited to): CPU-load, CPU clock frequency (i.e., "CPU speed"); level of memory usage; level of disk drive usage; depth of an input-output controller queue; a level of memory usage of the testing unit at the time of the calibration iteration (or stimulus response round); a level of disk drive usage of the testing unit at the time of the calibration iteration (or stimulus response round); a level of processor utilization at the time of the calibration iteration (or stimulus response round); a level of active processing threads of the processor at the time of the calibration iteration (or stimulus response round); a clock frequency of the processor at the time of the calibration iteration (or stimulus-response round); and a level of an input-output stack communication channel transmission rate of the testing unit at the time of the calibration iteration (or stimulus-response round); and/or the like.

Since calibration method 100C involves finding a large number of calibration latency values $L_{CAL}$, step 126 proceeds with querying whether all calibration iterations are completed, and if not, redirecting process flow back to step 122, wherein the next stimulus signal is generated. The calibration includes an optional step 128A of varying one or more latency modification parameters. Varying the latency modification parameters may comprise, without limitation, using software designed to stress and test CPU, memory, and I/O through a series of tests that include repeatedly performing specific mathematical operations, reading from and writing to memory, and reading from and writing to the disk drive. If all calibration iterations are completed, then method 100C continues with step 127, wherein a latency estimate $L_E$, corresponding to the testing unit 201, 250, is determined using the $L_{CAL}$ values determined from each of the foregoing calibration iterations. Step-127 determination may comprise taking a statistical mean, average, or median value of the $L_{CAL}$ values, binning the $L_{CAL}$ values into separate clusters based on additional factors, and/or the like.

Method 100C then proceeds to step 129 which involves determining an uncertainty value corresponding to testing unit 201, 250. Such an uncertainty value may generally comprise a metric representative of a width of the distribution of the $L_{CAL}$ values over the plurality of calibration iterations. The uncertainty may be positively correlated with the width of the $L_{CAL}$ distribution—i.e. higher uncertainty values corresponding to wider $L_{CAL}$ distributions and lower uncertainty values correspond to narrower $L_{CAL}$ distributions. In particular embodiments, the step 129 uncertainty value may comprise a variance of the $L_{CAL}$ distribution. In other embodiments, the step 129 uncertainty value may comprise a standard deviation of the $L_{CAL}$ distribution.

The step-127 determination of latency estimate $L_E$ based on the $L_{CAL}$ values may involve a process of "binning" (i.e., grouping according to a discrete plurality of value ranges) the $L_{CAL}$ values based upon the optional step-128 ascertained values of the latency modification parameters. Using CPU-load as an exemplary but non-limiting example of a "binning" variable, bin boundaries are determined based upon range of percentage CPU-loads—e.g., a first bin ranging from 0% CPU-load to 25% CPU-load, a second bin ranging from 25% CPU-load to 50% CPU-load, a third bin ranging from 51% CPU-load to 75% CPU-load, and a fourth bin ranging from 76% CPU-load to 100% CPU-load. After CPU-load is ascertained as the latency modification parameter in step 128, the corresponding latency calibration value $L_{CAL}$ is assigned to a corresponding "bin" of $L_{CAL}$ values. In each calibration iteration, an $L_{CAL}$ value is determined in step 125 and then binned according to the step-128 ascertained latency modification parameter value. In step 127, latency estimates $L_E$ are then determined for each bin. Each bin has a latency value $L_{CAL}$ distribution of its own, and statistical measures (e.g., average, mean, median value, etc.) may then be taken to determine a latency estimate $L_E$ for each bin in step 127, and the spread of the distribution (e.g., variance, standard deviation, etc.) may be determined in step 129 as the uncertainty for each bin. When the stimulus-response test is later administered (as in FIG. 1A), a latency modification parameter may be ascertained in connection with determining an estimated actual response time $RT_E$. Depending upon the value of the latency modification parameter, the value of step-113 latency estimate $L_E$ (FIG. 1A) may be determined (e.g., from a look-up table) based upon how the determined latency modification parameter would have been binned according the aforementioned procedure. Similarly, the step-103 uncertainty value (FIG. 1A) may also be determined (e.g., from another look-up table) according to the spread of $L_{CAL}$ values associated with the proper bin (i.e., the bin corresponding to the latency modification parameter ascertained during the stimulus-response round).

The multiple views of FIG. 4F illustrate how to determine latency estimate $L_E$ and associated uncertainty values in accordance with a particular alternative embodiment of the step-127 by defining a calibration function that correlates latency modification parameters with combined latency estimates $L_E$ and associated uncertainty values. In such embodiments, step-125 $L_{CAL}$ values (FIG. 1C) are determined on a testing unit 210, 252, while the testing units is subject to a broad range of latency modification parameters (for example, because the latency modification parameters are being deliberately manipulated; see e.g., steps 128A of FIG. 1C and 158A, 168A of FIG. 1D). A latency calibration function based on data-smoothing function 451, such as but not limited to a linear function (as shown), is used to regress the latency modification parameters to the plurality of measured $L_{CAL}$ values 453a-453n. In one non-limiting example, the parameters of the linear function can be found by minimizing the least-squared error between predicted calibration latency and measured calibration latency. The latency calibration function is then used to adjust latency estimates $L_E$ used during test administration (e.g. FIG. 1B, step 113). Likewise, a separate data-smoothing function 452, such as but not limited to a linear function (as shown), can be used as an uncertainty calibration function to regress the latency modification parameters with the measurement uncertainty. In one non-limiting example, the parameters of the linear function can be found by minimizing the least-squared error between the squared residual 454a-454n between measured latency and predicted latency from the measured $L_{CAL}$ values. The uncertainty calibration function is then used to adjust the uncertainty estimates used during test administration (e.g. FIG. 1A, step 103).

Figure 1D:
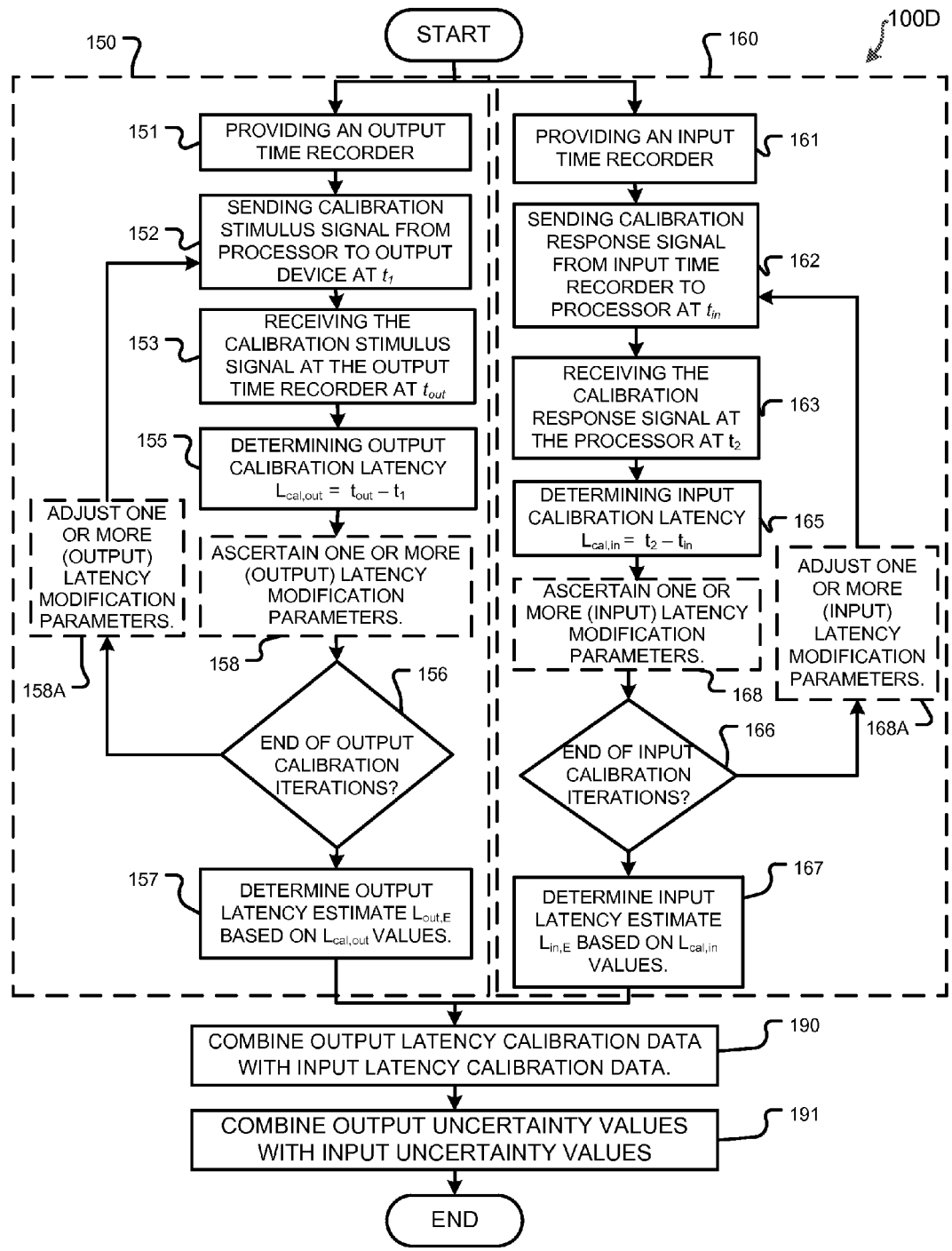
FIG. 1D contains a flow chart illustrating a method to determine a latency estimate $L_E$ for a testing unit using a two-phase calibration procedure to measure input latency separately from output latency, in accordance with a particular embodiment.

FIG. 1D provides a flowchart illustrating method 100D for a two-stage calibration process for calibrating a testing unit 201, 250 to determine an input latency value and an output latency value according to a particular embodiment. In some embodiments, the input latency and output latency values can be combined into a latency estimate $L_E$, according to a particular embodiment. Method 100D of the illustrated embodiment comprises two similar subprocesses. Output latency calibration subprocess 150 determines a value for the output latency estimate $L_{E,out}$ by measuring latency along only the output data path 215. Input latency calibration subprocess 160 determines a value for the input latency estimate $L_{E,in}$ by measuring latency along only the input data path 214.

Output latency calibration subprocess 150 commences in step 151, wherein an output time recorder is provided. The output time recorder may comprise a system configured to record the time at which electrical, audio, visual and/or pressure signals occur, e.g., a light sensor, audio sensor, or other stimulus sensor. In some embodiments an output time recorder may comprise an electrical sensor to detect when a calibration stimulus signal is sent from a processor to an output device, and a high speed camera to detect when a visual stimulus is presented by the output device. A number of steps may optionally be repeated throughout a number of output latency calibration iterations. For each such iteration, at a specific time, denoted $t_1$, in step 152 a calibration stimulus signal is sent from the processor to the output device. In step 153 the stimulus signal is received at the output time recorder at a specific time, denoted $t_{out}$. Step 155 proceeds by determining an output calibration latency $L_{cal,out}$ as the difference between $t_{out}$ and $t_1$ (i.e., $L_{cal,out}=t_{out}-t_1$). In particular embodiments, optional step 158 entails ascertaining one or more of the output latency modification parameters. Latency modification parameters may include (but are not limited to): CPU-load, CPU clock frequency (i.e., "CPU speed"); level of memory usage; level of disk drive usage; depth of an input-output controller queue; a level of memory usage of the testing unit at the time of the calibration iteration (or stimulus response round); a level of disk drive usage of the testing unit at the time of the calibration iteration (or stimulus response round); a level of processor utilization at the time of the calibration iteration (or stimulus response round); a level of active processing threads of the processor at the time of the calibration iteration (or stimulus response round); a clock frequency of the processor at the time of the calibration iteration (or stimulus-response round); and a level of an input-output stack communication channel transmission rate of the testing unit at the time of the calibration iteration (or stimulus-response round); and/or the like.

A test is then made to determine if all output latency calibration iterations are completed, in step 156. If not, flow is returned to step 152, and another output latency calibration iteration is commenced. Optionally in step 158A, prior to starting the next input latency calibration iteration, the latency modification parameters of the system can be varied based on the scheme described in step 128A. Once all output latency calibration iterations are completed, an output latency estimate $L_{out,E}$ is determined based upon one or more of the $L_{cal,out}$ values as measured during the output latency calibration iterations. In a particular embodiment, $L_{out,E}$ is determined as the expected value (e.g., mean, average, etc.) of values of $L_{cal,out}$ determined over a plurality of output latency calibration iterations.

Similarly, input latency calibration subprocess 160 proceeds in one or more input latency calibration iterations commencing in step 161, wherein an input time recorder is provided. The input time recorder may comprise a system configured to record the time at which electrical, audio, visual, movement, and/or pressure signals occur, e.g. a timer associated with a mechanical trigger, relay timer, optical sensor, Hall effect sensor, and/or the like. In some embodiments an input time recorder may comprise a motion sensor to detect when an input is received by an input device, and an electrical sensor to detect when an input signal is sent from the input device to a processor. Block 162 involves generating a calibration input signal at a specified time, denoted $t_{in}$, which may be measured by the step-161 input time recorder. The calibration input signal may be generated by any suitable manual or automated device. The calibration input signal is then received at the processor, in step 163, at time $t_2$. An input calibration latency $L_{cal,in}$ can then be determined in step 165 according to the formula $L_{cal,in}=t_2-t_{in}$. Optional step 168 may first be executed, in which case one or more input latency modification parameters may be modified before commencing the next input latency calibration iteration.

The conclusion of input latency calibration iterations are then tested in step 166. If more latency calibration iterations remain, flow proceeds back to step 162, wherein another calibration response signal is sent. Optionally in step 168A, prior to starting the next input latency calibration iteration, the latency modification parameters of the system can be varied based on the scheme described in step 128A. Once all input latency calibration iterations have been completed, flow passes to step 167 wherein an input latency estimate $L_{in,E}$ is determined based upon one or more of the $L_{cal,in}$ values as measured during the input latency calibration iterations. In a particular embodiment, $L_{in,E}$ is determined as the expected value (e.g., mean, average, etc.) of values of $L_{cal,in}$ determined over a plurality of input latency calibration iterations.

Output latency calibration data are then combined with input latency calibration data in step 190. Such combinations may comprise, without limitation, combinations based on the rules of probabilities and statistics, and overall latency is the addition of $L_{in,E}$ and $L_{out,E}$, wherein the sum is assigned to $L_E$. For those embodiments in which one or more latency modification parameters are adjusted during the calibration processes 100D, 150, 160, the latency calibration data may be binned or otherwise organized according to the values of the one or more latency modification parameters. In the non-limiting exemplary case of CPU-load adjustments being made during calibration processes 100D, 150, 160, (e.g., in steps 158A and 168A), it may be possible to organize the latency calibration data according to a specific set of CPU-load values or value ranges, e.g. percentage quartiles. All $L_{in,E}$ and $L_{out,E}$ values collected when the CPU-load was between 0% and 25% of maximum CPU capacity could be organized together, and, by way of non-limiting example, a latency estimate value for this CPU load range could be determined. Similar determinations could be made for the other quartiles of CPU-load capacity. Then, during stimulus-response test administration, CPU-load-specific values of $L_E$ could then be used as the step-113 latency offset, depending upon the CPU-load values at one or more times associated with the stimulus-response round under consideration.

Output uncertainty calibration data are then combined with the input uncertainty calibration data in step 191. Such combinations may comprise, without limitation, combinations based on the rules of probability and statistics, and the overall calibration variance is the sum of the input calibration variance, the output calibration variance, and the covariance between the input and output calibration latencies. When the covariance is zero the overall calibration variance is the sum of the input and output calibration variance. The overall calibration uncertainty, $U_E$ is the square root of the overall calibration variance. In general, the step 191 uncertainty is a metric representative of a width of the combined $L_{CAL,IN}$ and $L_{CAL,OUT}$ distributions. In some embodiments, this metric can be a variance and/or a standard deviation of the combined distribution.

In an alternative embodiment output calibration latency and input calibration latency are not combined in step 190. Instead, during test administration (e.g., method 100A of FIG. 1A) latency modification parameters are ascertained for estimated actual response times $RT_E$ corresponding to stimulus output and input response times such that each estimated actual response time has two corresponding latency estimates associated with it—one for the output latency estimate $L_{out,E}$ and one for the input latency estimate $L_{in,E}$. The input and output latency estimates $L_{out,E}$, $L_{in,E}$ are determined by the input and output latency modification parameters respectively. A latency look-up table based on binning the input and output latency parameters may be used, or separate input and output latency calibration functions may be used. The overall latency of the stimulus-response round $L_E$ is the sum of the input latency estimate $L_{in,E}$ and the output estimate $L_{out,E}$. Likewise, the associated uncertainty estimate of estimated actual response time $RT_E$ can be determined based on the input and output latency modification parameters either based on a uncertainty look-up table based on binning the input and output latency parameters, or based on separate input and output uncertainty calibration functions. The overall associated uncertainty is based on the combination of the input and output uncertainty estimates. In the non-limiting case where the uncertainty represents the variance, the overall associated input uncertainty is the sum of the input and output uncertainty estimates. In the case where the uncertainty represents the standard deviation, the overall uncertainty estimate is the square root of the variance estimate.

FIG. 2B provides a system diagram for a testing unit 250 as used in another particular embodiment. Testing unit 250 comprises a test controller 114, a stimulus output interface 222, and a response unit interface 226. Test controller 114 may comprise any suitable computing device or component capable of executing the instructions necessary to administer a stimulus-response test, such as a microprocessor, a device controller (with or without microcode), and/or the like. Stimulus output interface 222 may comprise any suitable device capable of interfacing test controller 114 with stimulus output device 256, such as an I/O controller, a device controller, and/or the like, and response unit interface 226 may comprise any suitable device capable of interfacing test controller 114 with response input device 260, such as an I/O controller, a device controller, and/or the like. Stimulus output device 256 is also shown, as is response input device 260. Stimulus output device 256 may comprise any suitable device for communicating a stimulus to the test taker 201, such as a monitor, video screen, loudspeaker, haptic feedback device, LED or LED panel, and/or the like, and response input device 260 may comprise any suitable device for receiving a response from test taker 210, such as a keyboard, mouse, joystick, game controller, push button, touch screen, microphone, camera, video camera, and/or the like.

Test controller 114 is configured to send a stimulus signal across data path 115 to stimulus output interface 222, which in turn is configured to send the stimulus signal across data path 224 to the stimulus output device 256. Stimulus output device 256 is configured to present test taker 201 with a stimulus 258. (Data path 115, stimulus output interface 222, and data path 224, when combined, are analogous to output data path 215 of FIG. 2A.) Response input device 260 is configured to receive a response 259 from test taker 201 and to send a response signal across data path 228 to the response input interface 226. Response input interface 226 is configured to send the response signal to the test controller 114 across data path 227. (Data path 228, response input interface 226, and data path 227, when combined, are analogous to input data path 214 of FIG. 2A.) Testing unit 250 also comprises optional components including, without limitation: a hard drive 216, memory 218, additional I/O ports 230, and a data link 233, which may be configured as a personal computer 252.

Figures 3A, 3B:
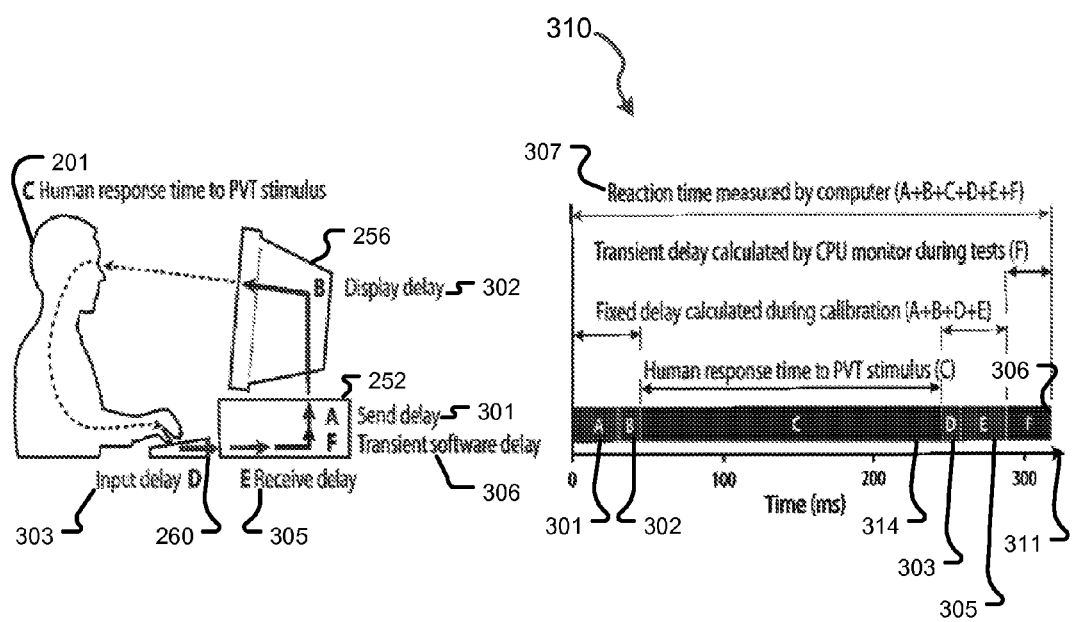
FIG. 3A depicts the sources of latency in a stimulus-response testing unit comprising a personal computer with common input and output devices, in accordance with a particular embodiment.
FIG. 3B is a timing diagram depicting the relationships between the different latencies in the FIG. 3A testing unit, in accordance with a particular embodiment.

FIG. 3A provides a diagram illustrating a number of the sources of latency associated with a testing unit, such as testing unit 252 (shown) or testing unit 210 (FIG. 2A), used in a particular embodiment. The testing unit as shown in FIG. 3A comprises a personal computer 252 with a built-in processor (not shown) capable of functioning as test controller 114, a stimulus output device 256 in the form of a computer display, and a response input device 260 in the form of a keyboard. The processor/test controller 114 is configured to send a stimulus signal to the stimulus output interface 222 (FIG. 2B). The resulting signal travel time may be referred to as the "send delay" 301, also denoted with the letter "A" in the FIG. 3 graphic. The stimulus output interface 122 is configured to send the stimulus signal to the output device 256, which in turn is configured to provide a stimulus (not shown) to test taker 201. The travel time from stimulus-output interface 222 to test taker 201 may be referred to as the "display delay" 302, also denoted with the letter B in the FIG. 3 graphic. When combined, the send delay 301 and the display delay 302 may be considered the "output latency time" associated with the output data path 215 (FIG. 2A).

Test taker 201 may respond to the visual stimulus and provide an input response at response input interface 260 (via the keyboard 303). Response input device 260 may also have an associated latency, identified in FIG. 3A as the "input delay" 303, denoted with the letter "D." Input delay 303 may be caused by such phenomena (without limitation) as a long or slow keyboard polling rate, lack of responsiveness by the keys on the keyboard (or buttons on the mouse, etc.), signal travel time from the keyboard to the keyboard controller or other I/O controller associated with computer 252, and/or the like. It will be appreciated that the specific nature of input delay 303 will depend upon the specific nature of response input device 260 Further, "receive delay" 305 represents an additional latency (identified with the letter "E") associated with processing the signal once received from response input device 260 at computer 252. Receive delay 305 may be associated with such phenomena as an I/O buffer or controller, internal signal travel time inside computer 252, and/or the like. Another latency 306 referred to as the "transient software delay" and denoted with the letter "F" in FIG. 3A is associated with increased demands on the processor (e.g., CPU-load, memory usage, disk drive usage, I/O controller usage, and/or the like) caused by software processes extraneous to the stimulus-response test being administered. When combined, the input delay 303, the receive delay 305, and the transient software delay 306 may be considered the "input latency time" associated with the input data path 214 (FIG. 2A). In some circumstances, however, "transient software delay" 306 may also cause increased demands on the processor (e.g., CPU-load, memory usage, disk drive usage, I/O controller usage, and/or the like) stemming from software processes extraneous to the stimulus-response test being administered. In such circumstances, these increased processor demands may also have an impact on the output latency time. The output latency time should therefore be understood possibly to include such transient software delays where applicable.

FIG. 3B provides a timeline 310 for understanding the accumulated effect of the several latencies discussed in connection with FIG. 3A. Specifically timeline 310 comprises an x-axis indicating the round-trip signal time $T_{RTS}$ (in ms.)—i.e., the overall time between time $t_1$ that a stimulus signal is sent from the processor to the time $t_2$ that a response signal is detected at the processor for a given stimulus-response round. In the case illustrated in timeline 310, the round-trip signal time 307 (elsewhere denoted $T_{RTS}$) lies just over 300 ms. Round-trip signal time 307 comprises the sum of latencies identified in FIG. 3A—i.e. latencies 301, 302, 303, 304, 305, 306 (alternatively identified in FIGS. 3A and 3B as latencies A, B, D, E, and F)—along with the actual response time 314 (identified as latency C in FIGS. 3A and 3B). Actual response time 314 comprises the duration between the time that the stimulus is presented to the test taker 201 by the output device 256 and the time that the test taker 201 responds at the input device 260.

Figure 3C:
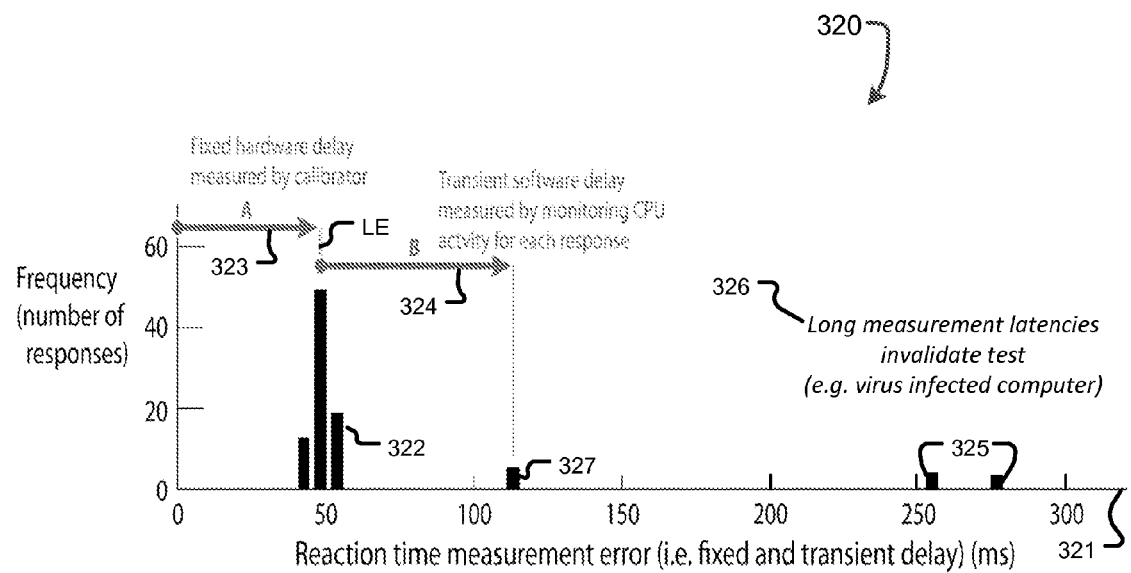
FIG. 3C is an example histogram representative of latency measurements associated with stimulus-response rounds plotted as a function of latency magnitude (in ms.)

FIG. 3C provides a latency measurement histogram 320 depicting the number of measured latencies graphed according to the total latency magnitude (i.e., the sum of input latency and output latency) on time axis 321. The FIG. 3C data may be obtained, for example, by a calibration process (e.g. methods 100C or 100D of FIG. 1C or 1D, respectively) executed on a testing system. Histogram 320 depicts a cluster 322 of measured latencies in approximately the 50±5 ms range. Cluster 322 is indicative of typical fixed hardware latencies (i.e., latencies A, B, D, E, and F from FIG. 3A) when no transient software delay is present. For example, the latencies in cluster 322 are typical of the (non-limiting) case when no software processes (other than the stimulus-response test software) are consuming the resources of processor 211 and/or test controller 114. A statistical measure, such as an average or mean value, etc., of all the measured latencies of histogram 320 (or, in an alternative embodiment, just cluster 322) can provide a typical latency estimate $L_E$. Such a latency estimate $L_E$ may be used as step-113 offset (FIG. 1B) from the round-trip signal time 307 of FIG. 3B to account for the delay associated with the testing unit 210, 250 (or, in the aforementioned alternative embodiment, just the hardware components of the testing unit 210, 250, exclusive of transient software delays 306). It can be seen from FIG. 3C that another cluster 327 of latency measurements occurs at just over 100 ms in histogram 320. Cluster 327 may represent latency measurements caused by two components: the fixed hardware delay (denoted by the interval A in FIG. 3C), and by transient software delays 306 (denoted by the interval B in FIG. 3C)—e.g., heavy CPU load causing the test-administration code to execute more slowly than usual. In the FIG. 3C example, a third cluster 325 of latency measurements occurs on time axis 321 just over the 250 ms mark. Cluster 325 may indicate delays of such duration as to bring validity of the test results into question—e.g., because of a virus-infected computer, or the existence of a large number of non-test software processes, and/or the like.

The multiple views of FIG. 3D provide a series of latency histograms 360 (FIG. 3D-I), 380 (FIG. 3D-II), 390 (FIG. 3D-III) depicting the number of measured input latencies, output latencies, and combined latencies, respectively, graphed according to their magnitude on time axis 321. The FIG. 3D data may be obtained, for example, by a modified, two-part calibration process, similar to calibration method 100C, but wherein input latencies are measured separately from output latencies. FIG. 3D-I provides and input latency histogram 360 and illustrates several clusters 362, 365, 367 of calibration latency values measured during a calibration process executed on a testing unit 201, 250 involving separate measurement of input latency values. Similarly, FIG. 3D-II provides output latency histogram 380 and illustrates several clusters 382, 385, 387 of calibration latency values measured during a calibration process executed on the testing unit 201, 250 involving separate measurement of output latency values. Latency clusters 362 and 382 may be analogous to latency cluster 322 of FIG. 3C; latency clusters 365, 385 may be analogous to latency cluster 327 of FIG. 3C; and latency clusters 367, 387 may be analogous to latency cluster 325 of FIG. 3C. FIG. 3D-III provides a combined latency histogram 390 and illustrates several clusters 392, 395, 397 of calibration latency values ascertained by combining the calibration latency values of input latency histogram 360 and output latency histogram 380. In a particular embodiment, the combination of data from input latency histogram 360 and data from output latency histogram 380 comprises adding pairs of measured input latency values and output latency values for those circumstances wherein the input latency values are measured at the same time or under the same conditions as the output latency values. In another particular embodiment, the combination of data from input latency histogram 360 and data from output latency histogram 380 comprises adding the mean value of the input latency histogram 360 to the mean value (alternatively, median, average, and/or any other statistical measure indicative of the clusters' central value) of the output latency histogram 380 to determine the mean value of combined latency histogram 390, and may further comprise adding the spread or width (e.g., variance, standard deviation, and/or the like) of input histogram 360 with the spread or width of output histogram 380 to determine the spread or width of combined latency histogram 390.

Figure 4A:
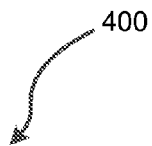
FIG. 4A provides a table of exemplary estimated actual response times $RT_E$, associated uncertainty values, primary and secondary classifications, and associated confidence values comprising the probability that the response time is properly classified in the primary and secondary classifications, respectively, for a particular administration of a stimulus-response test, in accordance with a particular embodiment.

FIG. 4A provides a chart 400 illustrating how a set of estimated actual response times may be classified according to established testing protocols into response-type categories based upon the magnitude of the estimated actual response time $RT_E$ and of how a confidence value may be associated with the classification based upon the uncertainty value associated with the estimated actual response time $RT_E$. Column 401 (labeled "Response Time") contains estimated actual response times $RT_E$ as measured by step 102 of method 100A and/or step 113 of method 100B (FIGS. 1A and 1B, respectively) during the administration of a stimulus-response test. Column 402 (labeled "Uncertainty") contains uncertainty values associated with each of the estimated actual response times $RT_E$ of column 401 as determined in step 103 of method 100A (FIG. 1A), step 129 (FIG. 1C), and/or step 191 (FIG. 1D).

One output of a stimulus-response test, according to some embodiments, is a performance indicator that may be based on one or more estimated actual response times $RT_E$. An example of a performance indicator is a selection of one performance level (classification) among a plurality of discrete performance levels (classifications). In some embodiments the selection of such performance levels (classifications) may be based on a rule according to the estimated actual response time $RT_E$. For example, according to some testing protocols used with the PVT, the classification may be a "false start" if $RT_E \leq 0$; a "coincident false start" if $0 < RT_E \leq th_1$; a "fast" response if $th_1 < RT_E \leq th_2$; a "slow" response if $th_2 < RT_E \leq th_3$; a "lapse" if $th_3 < RT_E \leq th_4$; and a "timeout" if $RT_E \geq th_4$, where $th_1 < th_2 < th_3 < th_4$, and where $th_1$, $th_2$, $th_3$, $th_4$ are thresholds that may be pre-configured or configured for particular circumstances. The selection of performance levels (classifications) may occur for each stimulus-response round of a stimulus-response test and/or there may be one overall performance level.

Column 403 (labeled "Primary Classification") contains a primary classification assigned to the estimated actual response times $RT_E$ of a particular stimulus-response round, which may be selected in accordance with a rule of the type described above. Column 404 contains a confidence rating (such as a percentage probability) associated with each of the primary classifications of column 403. Column 405 contains optional secondary classifications of the column-401 estimated actual response times $RT_E$.

Where the column-402 uncertainty with a particular column-401 estimated actual response time $RT_E$ is such that the column-401 estimated actual response time $RT_E$ could be classified into a difference performance level (classification), then this "secondary" performance level (classification) is reflected in column 405. Column 406 may reflect a confidence ration (such as a percentage probability) associated with the column-405 secondary classification.

Response No. 1, by way of non-limiting example, has a column-403 primary classification as a "fast" response and a column-405 secondary classification as a "slow" response, with each classification having an associated confidence value as reflected in columns 404 and 406, respectively, as 98.9% and 1.1%. It will be appreciated that in some circumstances of relatively high uncertainty, there may be more than two possible performance classifications associated with confidence values. Methods for determining the associated confidence value are discussed, below, in connection with FIG. 4E.

The multiple views of FIG. 4E illustrate how to calculate the primary and secondary confidence values 404, 406 associated with the primary and secondary classifications 403, 405 as discussed in connection with FIG. 4A. An estimated actual response time $RT_E$ 441 is shown on timeline 442. An uncertainty range 445 is shown ranging from time $RT_E - U$ to $RT_E + U$, where U represents the uncertainty value associated with the estimated actual response time $RT_E$. Response time boundaries $th_1$, $th_2$, and $th_3$ (444a, 444b, and 444c) represent the time thresholds dividing different score classifications according to particular testing protocols (see, e.g., discussion of discrete performance levels/classifications for the PVT in connection with FIG. 4A, above). For convenience, it will be assumed (without limitation) in the present discussion that the region between time threshold $th_1$ 444a and time threshold $th_2$ 444b corresponds to a "fast" response on the PVT, and that the region between time threshold $th_2$ 444b and time threshold $th_3$ 444c corresponds to a "slow" response on the PVT.

For FIG. 4E-I an assumption is made that the probability of locating the actual response time within error range 445 is uniformly distributed across the error range 445, as illustrated by uniform probability distribution curve 460. The column-404 primary confidence value thereby corresponds to the percentage of the error range 445 (which has a length of $2f(U)$, where $f$ is a function used to address different statistical measures of a normal distribution's width or spread— e.g., variance $\sigma^2$, standard deviation $\sigma$, and/or the like) within the primary classification region. Similarly, the column-406 secondary confidence value corresponds to the percentage of the error range 445 within the secondary classification region. If $P_1$ represents the column-404 primary confidence value, and if $P_2$ represents the column-406 secondary confidence value, under the values of $RT_E$ and U shown in FIG. 4E-I these probabilities amount to: $P_1 = (th_2 - (RT_E - f(U)))/2f(U)$ and $P_2 = ((RT_E + f(U)) - th_2)/2f(U)$. In the case where the uncertainty U represents the standard deviation, $f(U) = \sqrt{3} U$.

Similarly, FIG. 4E-II assumes that the probability of locating the actual response time amounts to a normal distribution 450 centered about the estimated actual response time $RT_E$ and with a spread (e.g., variance, standard deviation, etc.) equal to the uncertainty value $f(U)$. In such a case, the column-404 primary confidence value equals the percentage of the area under normal distribution 450 lying within the column-403 primary classification region, and the column-406 secondary confidence value equals the percentage of the area under the normal distribution 405 lying within the column-405 secondary classification region. If $P_1$ represents the column-404 primary confidence value, and if $P_2$ represents the column-406 secondary confidence value, under the values of $RT_E$ and U shown in FIG. 4E-II these probabilities amount to:

$$P_1 = \int_{th_1}^{th_2} N(x: M=RTE, \sigma=f(U))dx, \text{ and} \qquad \text{Eqn. 1}$$

$$P_2 = \int_{th_2}^{th_3} N(x: M=RTE, \sigma=f(U))dx, \qquad \text{Eqn. 2}$$

where N signifies the normal distribution, M signifies the median value of the normal distribution N, and $\sigma$ represents the standard deviation of the normal distribution N. In the case where the uncertainty U represents a standard deviation, then the function, $f(U) = U$.

Figure 4B:
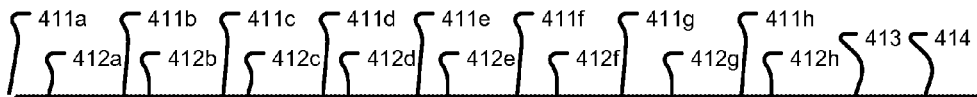
FIG. 4B provides a set of stimulus-response test metrics and associated confidence values comprising the metric uncertainty, for five (5) sample administrations of stimulus-response tests, in accordance with a particular embodiment.
Figure 4B:
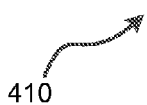

Another example of a performance indicator that may be output from a stimulus-response test is a test metric. Test metrics may be calculated from one or more values of the estimated actual response times $RT_E$. In some embodiments test metrics may be output on a per test basis. In some embodiments, test metrics may be output on a per stimulus-response round basis. FIG. 4B is a table 410 of sample test metrics 411a through 411h and associated confidence values (in the form of uncertainty values associated with each test metric) 412a through 412h for a set of five (5) separate stimulus-response tests. In table 410 of FIG. 4B, the test metrics of each row are metrics associated with a plurality of estimated actual response times $RT_E$, determined during the administration of a stimulus-response test involving a corresponding plurality of stimulus-response rounds. Examples of test metrics illustrated in table 410 include: mean estimated actual mean response times (MeanRT) 411a; standard deviation of estimated actual response times (STDRT) 411b; mean of the fastest ten-percent of estimated actual response times (MeanFRT) 411c; mean of the slowest ten-percent of mean actual response times (MeanSRT) 411d; number of lapses during test (Lapses) 411e; number of timeouts during test (Timeouts) 411f; mean of the reciprocal estimated actual response times (i.e., 1 divided by the estimated actual response time) (MeanRRT) 411g; and the standard deviation of the mean reciprocal estimated actual response times (STDMeanRRT) 411h. Associated uncertainties 412a, 412b, 412c, 412d, 412e, 412f, 412g, 412h, respectively, are illustrated in table 410 alongside their corresponding metric. Equations for determining the associated uncertainties 412a-412h based on the uncertainty in the values of the estimated actual response times $RT_E$ can be found in table 430 of FIG. 4D, discussed below. It will be appreciated that the metrics of FIG. 4B are exemplary and non-limiting and that other suitable metrics could be determined. Another example of a performance indicator that may be output from a stimulus-response test is an overall test result (e.g., pass vs. fail). Table 410 (FIG. 4B) also has a column for overall test result 413 and an associated confidence value 414 related to the test result 413. The test result may be based on a mathematical combination or function of one or more of the test metrics 412a-412h.

Figure 4C:
FIG. 4C provides a table illustrating possible test results (e.g., pass vs. fail) and associated confidence values comprising a probability the reported test outcome is accurate, in accordance with a particular embodiment.
Figure 4C:

FIG. 4C provides a punnett square 420 illustrating the possible combinations of test result 413 (e.g., pass vs. fail, in a particular embodiment), and confidence value associated 414 with the test result 413. Punnet square 420 divides confidence values into two (2) categories: "sure" or "confident" values; and "possible," "not sure," or "probability" values. The sure/confident uncertainty category reflects the fact that under some testing circumstances, the uncertainty values associated with the plurality of estimated actual response times determined during a stimulus-response test are of such magnitudes that there is no possibility (or, alternatively, only a negligible or suitably small possibility—e.g., in comparison to a minimum threshold), that the test result could be other than of one value. Otherwise (e.g., if the associated uncertainty values admit the possibility of more than one test result), the test result is reported as "not sure" or "possible." In some embodiments, not shown, possible test results may be returned with an assigned probability rating based upon determinations involving the uncertainty values. Other embodiments may include test results 413 with more than two values—e.g., a test result comprising a score in one of ten distinct deciles on a test, a test result comprising an assignment of typical academic-style letter grades (i.e., A, B, C, D, F), and/or the like.

FIG. 4D provides a chart 430 containing mathematical formulas used to determine a set of test metrics and the uncertainty values associated with those test metrics based on estimated actual response times $RT_E$ (indicated to be $x_n$ in FIG. 4D) and their corresponding uncertainty values (indicated to be $u_n$ in FIG. 4D), in accordance with a particular embodiment. Column 432 (labeled "metric name") identifies six (6) non-limiting exemplary test metrics by name, in accordance with the discussion provided in connection with FIG. 4A (see test metrics 411a-411h). Column 432 (labeled "metric description") provides a brief explanation of each of the non-limiting exemplary test metrics from column 431. Column 433 (labeled "equation for the metric") provides mathematical equations for determining the test metrics of column 431 using the estimated actual response times ($RT_E$, $x_n$). Column 434 (labeled "equation for the metric uncertainty") provides equations for determining the confidence values associated with each of the test metrics of column 431 based on the step-103 (FIG. 1A) uncertainty values ($u_n$) associated with the plurality of estimated actual response times ($RT_E$, $x_n$) determined during the administration of a stimulus-response test. For some test metrics, e.g., mean reciprocal of reaction times, the column-434 equation for the metric uncertainty may also be based on the plurality of estimated actual response times ($RT_E$, $x_n$).

Certain implementations of the invention comprise computer processors which execute software instructions which cause the processors to perform a method of the invention. For example, one or more processors may implement data processing steps in the methods described herein by executing software instructions retrieved from a program memory accessible to the processors. The invention may also be provided in the form of a program product. The program product may comprise any medium which carries a set of computer-readable instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs and DVDs, electronic data storage media including ROMs, flash RAM, or the like. The instructions may be present on the program product in encrypted and/or compressed formats.

Certain implementations of the invention may comprise transmission of information across networks, and distributed computational elements which perform one or more methods of the inventions. For example, response times may be delivered over a network, such as a local-area-network, wide-area-network, or the internet, to a different computational device that scores the response times. Such a system may enable a distributed team of operational planners and monitored individuals to utilize the information provided by the invention. Such a system would advantageously minimize the need for local computational devices.

Certain implementations of the invention may comprise exclusive access to the information by the individual subjects. Other implementations may comprise shared information between the subject's employer, commander, flight surgeon, scheduler, or other supervisor or associate, by government, industry, private organization, etc., or any other individual given permitted access.

Certain implementations of the invention may comprise the disclosed systems and methods incorporated as part of a larger system to support rostering, monitoring, diagnosis, epidemiological analysis, selecting or otherwise influencing individuals and/or their environments. Information may be transmitted to human users or to other computer-based systems.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e. that is functionally equivalent), including components which are not structurally equivalent to the disclosed structure which performs the function in the illustrated exemplary embodiments of the invention.

It will be apparent to those skilled in the art in the light of the foregoing disclosure, many alterations and modifications are possible in the practice of this invention without departing from the spirit or scope thereof. For example:

Purely analytical examples or algebraic solutions should be understood to be included;

In addition to the meanings set forth in the forgoing discussion, the term "latency modification parameter may include (without limitation): a level of memory usage of the testing unit at the time of the calibration iteration (or stimulus response round); a level of disk drive usage of the testing unit at the time of the calibration iteration (or stimulus response round); a level of processor utilization at the time of the calibration iteration (or stimulus response round); a level of active processing threads of the processor at the time of the calibration iteration (or stimulus response round); a clock frequency of the processor at the time of the calibration iteration (or stimulus response round); and a level of an input-output stack communication channel transmission rate of the testing unit at the time of the calibration iteration (or stimulus response round); and In alternate embodiments of the foregoing invention disclosed herein, latency estimate LE and the associated uncertainty values may be ascertained for one or more testing units 210, 252 and then applied to similar testing units having similar hardware and/or software components, and such latency estimate values LE and associated uncertainty values may be conveniently stored in a look-up table and/or other similar database.

Accordingly it is intended that the appended claims and any claims hereafter introduced are interpreted to include all such modifications, permutations, additions, and sub-combinations as are within their broadest possible interpretation.

What is claimed is:

1. A processor-based method for scoring a stimulus-response test for a test taker with a confidence value based on response-time measurement uncertainty, the method comprising:

providing a testing unit, the testing unit comprising: a processor, an input device accessible to a test taker, an output device accessible to the test taker, an output data path connecting the processor to the output device, and an input data path connecting the input device to the processor;

administering, with the testing unit, a stimulus-response test to the test-taker, administering the stimulus-response test comprising conducting a plurality of stimulus-response rounds, each of the plurality of stimulus-response rounds comprising:
sending a stimulus signal from the processor to the output device via the output data path, the stimulus signal sent from the processor at a first time $t_1$, the stimulus signal causing the output device to output a stimulus and prompting the test taker to respond to the stimulus at the input device;
receiving a response signal from the input device at the processor via the input data path, the response signal received at the processor at a second time $t_2$;
determining, with the processor, a round-trip signal time $T_{RTS}$ comprising a time interval between the first and second times;
determining, with the processor, an estimated actual response time $RT_E$ to be a difference between the round trip signal time $T_{RTS}$ and a latency estimate $L_E$, the latency estimate $L_E$ representing an estimate of a combination of: an output latency time between the first time $t_1$ and a time that the stimulus is output from the output device; and an input latency time between a time that the test taker responds to the stimulus at the input device and the second time $t_2$;

determining, with the processor, one or more uncertainty values representing uncertainty associated with the plurality of estimated actual response times $RT_E$;
determining, with the processor, a performance indicator for the test taker, the performance indicator based on the plurality of estimated actual response times $RT_E$; and
determining, with the processor, a confidence value, the confidence value based on the one or more uncertainty values and representative of a confidence in the performance indicator.

2. A method according to claim 1 comprising performing a calibration operation to determine the latency estimate $L_E$, performing the calibration operation comprising:

providing an automatic responder, the automatic responder configured to respond to a calibration stimulus output from the output device by inputting a calibration response at the input device at an automatic response time $T_{RA}$ after the output of the calibration stimulus from the output device;

for a plurality of calibration iterations:
sending a calibration stimulus signal from the processor to the output device via the output data path, the calibration stimulus signal sent from the processor at a first calibration time, the calibration stimulus signal causing the output device to output a calibration stimulus and prompting the automatic responder to respond to the calibration stimulus at the input device;
receiving a calibration response signal from the input device at the processor via the input data path, the calibration response signal received at the processor at a second calibration time;
determining, with the processor, a calibration round-trip signal time $T_{CAL,RTS}$ comprising a time interval between the first and second calibration times;
determining, with the processor, the calibration latency $L_{CAL}$ to be the difference between the calibration round-trip signal time $T_{CAL,RTS}$ and the automatic response time $T_{RA}$; and determining, with the processor, the latency estimate $L_E$ to be a statistical mean of the calibration latencies $L_{CAL}$ over the plurality of calibration iterations.

3. A method according to claim 2 wherein determining one or more uncertainty values comprises determining an uncertainty value based on a metric representative of a width of a distribution of calibration latencies $L_{CAL}$ over the plurality of calibration iterations.

4. A method according to claim 3 wherein the metric representative of the width of the distribution of calibration latencies $L_{CAL}$ over the plurality of calibration iterations comprises at least one of: a statistical variance of the calibration latencies $L_{CAL}$ over the plurality of calibration iterations; a statistical standard deviation of the calibration latencies $L_{CAL}$ over the plurality of calibration iterations; bounds of an assumed uniform distribution of the calibration latencies $L_{CAL}$ over the plurality of calibration iterations.

5. A method according to claim 2 wherein determining one or more uncertainty values comprises:

determining, with the processor, a base uncertainty value based on a metric representative of a width of a distribution of calibration latencies $L_{CAL}$ over the plurality of calibration iterations; and determining, with the processor, an uncertainty value for each of the plurality of stimulus-response rounds, wherein determining the uncertainty value for each stimulus-response round comprises:

ascertaining, with the processor, a round-specific value of a latency modification parameter at a time associated with the stimulus response round; and adjusting, with the processor, the base uncertainty value based on the round-specific value of the latency modification parameter to obtain the uncertainty value for the stimulus-response round.

6. A method according to claim 5 wherein the round-specific value of the latency modification parameter is representative of a load of the processor at the time of the stimulus-response round.

7. A method according to claim 2 comprising repeating the step of administering the stimulus-response test for a plurality of stimulus-response tests administered to one or more test-takers and using the same latency estimate $L_E$ for each of the plurality of stimulus-response tests.

8. A method according to claim 1 comprising performing a calibration operation comprising:

providing an automatic responder, the automatic responder configured to respond to a calibration stimulus output from the output device by inputting a calibration response at the input device at an automatic response time $T_{RA}$ after the output of the calibration stimulus from the output device;

for a plurality of calibration iterations:

sending a calibration stimulus signal from the processor to the output device via the output data path, the calibration stimulus signal sent from the processor at a first calibration time, the calibration stimulus signal causing the output device to output a calibration stimulus and prompting the automatic responder to respond to the calibration stimulus at the input device;

receiving a calibration response signal from the input device at the processor via the input data path, the calibration response signal received at the processor at a second calibration time;

determining, with the processor, a calibration round-trip signal time $T_{CAL,RTS}$ comprising a time interval between the first and second calibration times;

determining, with the processor, the calibration latency $L_{CAL}$ to be the difference between the calibration round-trip signal time $T_{CAL,RTS}$ and the automatic response time $T_{RA}$;

ascertaining, with the processor, a value of a latency modification parameter at a time associated with the calibration iteration; and separating, with the processor, the values of the latency modification parameter into a plurality of parameter value bins and for each parameter value bin:

determining, with the processor, a parameter value adjusted latency estimate $L_{E,PARAM}$ to be a statistical mean of the calibration latencies $L_{CAL}$ over any calibration iterations having latency modification parameter values in the parameter value bin; and determining, with the processor, a parameter value adjusted uncertainty value based on a metric representative of a width of a distribution of calibration latencies $L_{CAL}$ over the calibration iterations having latency modification parameter values in the parameter value bin.

9. A method according to claim 8 wherein each of the plurality of stimulus response rounds comprises:

ascertaining, with the processor, a round-specific value of the latency modification parameter at a time associated with the stimulus response round; and determining, with the processor, the latency estimate $L_E$ by: selecting a parameter value bin according to the round-specific value of the latency modification parameter; and determining the latency estimate $L_E$ to be the parameter value adjusted latency estimate $L_{E,PARAM}$ associated with the selected parameter value bin.

10. A method according to claim 9 wherein determining the one or more uncertainty values comprises, for each of the plurality of stimulus response rounds, determining a corresponding uncertainty value by: selecting a parameter value bin according to the round-specific value of a latency modification parameter; and determining the corresponding uncertainty value to be the parameter value adjusted uncertainty value associated with the selected parameter value bin.

11. A method according to claim 9 wherein the round-specific value of the latency modification parameter is representative of one or more of: a load of the processor at the time of the stimulus-response round; a level of memory usage of the testing unit during the stimulus-response round; a level of disk drive usage of the testing unit during the stimulus-response round; a level of active processing threads of the processor at the time of the stimulus-response round; a clock frequency of the processor at the time of the stimulus-response round; and a level of an input-output stack communication channel transmission rate of the testing unit during the stimulus-response round.

12. A method according to claim 8 wherein the value of the latency modification parameter is representative of one or more of: a load of the processor at the time of the calibration iteration; a level of memory usage of the testing unit at the time of the calibration iteration; a level of disk drive usage of the testing unit at the time of the calibration iteration; a level of active processing threads of the processor at the time of the calibration iteration; a clock frequency of the processor at the time of the calibration iteration; and a level of an input-output stack communication channel transmission rate of the testing unit at the time of the calibration iteration.

13. A method according to claim 8 wherein each of the plurality of calibration iterations comprises adjusting the latency modification parameter at the time associated with the calibration iteration.

14. A method according to claim 13 wherein adjusting the latency modification parameter comprises using software designed to stress one or more of: the processor, the interaction of the processor with memory and the interaction of the processor with one or more I/O devices.

15. A method according to claim 1 comprising performing a calibration operation to determine a base latency estimate, performing the calibration operation comprising:

providing an automatic responder, the automatic responder configured to respond to a calibration stimulus output from the output device by inputting a calibration response at the input device at an automatic response time $T_{RA}$ after the output of the calibration stimulus from the output device;

for a plurality of calibration iterations:

sending a calibration stimulus signal from the processor to the output device via the output data path, the calibration stimulus signal sent from the processor at a first calibration time, the calibration stimulus signal causing the output device to output a calibration stimulus and prompting the automatic responder to respond to the calibration stimulus at the input device;

receiving a calibration response signal from the input device at the processor via the input data path, the calibration response signal received at the processor at a second calibration time;

determining, with the processor, a calibration round-trip signal time $T_{CAL,RTS}$ comprising a time interval between the first and second calibration times;

determining, with the processor, the calibration latency $L_{CAL}$ to be the difference between the calibration round-trip signal time $T_{CAL,RTS}$ and the automatic response time $T_{RA}$; and determining, with the processor, the base latency estimate to be a statistical mean of the calibration latencies $L_{CAL}$ over the plurality of calibration iterations;

determining, with the processor, a latency estimate $L_E$ for each of the plurality of stimulus-response rounds, wherein determining the latency estimate $L_E$ for each stimulus-response round comprises:

ascertaining, with the processor, a round-specific value of a latency modification parameter at a time associated with the stimulus response round; and adjusting, with the processor, the base latency estimate based on the round-specific value of the latency modification parameter to obtain the latency estimate $L_E$ for the stimulus-response round.

16. A method according to claim 15 wherein the round-specific value of the latency modification parameter is representative of a load of the processor at the time of the stimulus-response round.

17. A method according to claim 1 comprising performing a calibration operation to determine the latency estimate $L_E$, performing the calibration operation comprising:

for a plurality of output calibration iterations:
measuring, with the processor, the output latency of a calibration stimulus signal sent from the processor to the output device via the output data path;

for a plurality of input calibration iterations:
measuring, with the processor, the input latency of a calibration response signal sent from the input device to the processor via the input data path; and determining, with the processor, the latency estimate $L_E$ to be a sum of a statistical mean of the measured output latencies over the plurality of output calibration iterations and a statistical mean of the measured input latencies over the plurality of input calibration iterations.

18. A method according to claim 17 wherein determining one or more uncertainty values comprises determining an uncertainty value based on a metric representative of a width of a combined distribution, the combined distribution comprising a combination of an input distribution of the measured input latencies over the plurality of input calibration iterations and an output distribution of the measured output latencies over the plurality of output calibration iterations.

19. A method according to claim 17 wherein determining one or more uncertainty values comprises determining an uncertainty value based on at least one of: a sum of a statistical variance of the measured output latencies over the plurality of output calibration iterations and a statistical variance of the measured input latencies over the plurality of input calibration iterations; and a square root of a sum of the statistical variance of the measured output latencies over the plurality of output calibration iterations and the statistical variance of the measured input latencies over the plurality of input calibration iterations.

20. A method according to claim 17 wherein determining one or more uncertainty values comprises:

determining, with the processor, a base uncertainty value based on a metric representative of a width of a combined distribution, the combined distribution comprising a combination of an input distribution of the measured input latencies over the plurality of input calibration iterations and an output distribution of the measured output latencies over the plurality of output calibration iterations; and determining, with the processor, an uncertainty value for each of the plurality of stimulus-response rounds, wherein determining the uncertainty value for each stimulus-response round comprises:

ascertaining, with the processor, a round-specific value of a latency modification parameter at a time associated with the stimulus response round; and adjusting, with the processor, the base uncertainty value based on the round-specific value of the latency modification parameter to obtain the uncertainty value for the stimulus-response round.

21. A method according to claim 17 wherein performing the calibration operation comprises, for each output calibration iteration:
ascertaining, with the processor, a value of a latency modification parameter at a time associated with the output calibration iteration;

for each input calibration iteration:
ascertaining, with the processor, a value of a latency modification parameter at a time associated with the output calibration iteration;

separating, with the processor, the values of the latency modification parameter into a plurality of parameter value bins and for each parameter value bin:

determining, with the processor, a parameter value adjusted latency estimate $L_{E,PARAM}$ to be a statistical mean of the sum of the measured output latencies over any output calibration iterations having latency modification parameter values in the parameter value bin and the measured input latencies of any input calibration iterations having latency modification parameter values in the parameter value bin; and determining, with the processor, a parameter value adjusted uncertainty value based on a metric representative of a width of a combined distribution, the combined distribution comprising a combination of an input distribution of the measured input latencies over any input calibration iterations having latency modification parameter values in the parameter value bin and an output distribution of the measured output latencies over any output calibration iterations having latency modification parameter values in the parameter value bin.

22. A method according to claim 21 wherein each of the plurality of stimulus response rounds comprises:

ascertaining, with the processor, a round-specific value of a latency modification parameter at a time associated with the stimulus response round; and determining, with the processor, the latency estimate $L_E$ by: selecting a parameter value bin according to the round-specific value of the latency modification parameter; and determining the latency estimate $L_E$ to be the parameter value adjusted latency estimate $L_{E,PARAM}$ associated with the selected parameter value bin.

23. A method according to claim 22 wherein determining the one or more uncertainty values comprises, for each of the plurality of stimulus response rounds, determining a corresponding uncertainty value by: selecting a parameter value bin according to the round-specific value of the latency modification parameter; and determining the corresponding uncertainty value to be the parameter value adjusted uncertainty value associated with the selected parameter value bin.

24. A method according to claim 17 determining the one or more uncertainty values comprises:

determining, with the processor, a base uncertainty value based on a metric representative of a width of a combined distribution, the combined distribution comprising a combination of an input distribution of the measured input latencies over the plurality of input calibration iterations and an output distribution of the measured output latencies over the plurality of output calibration iterations;

determining, with the processor, an uncertainty value for each of the plurality of stimulus-response rounds, wherein determining the uncertainty value for each of the plurality of stimulus-response rounds comprises:

ascertaining, with the processor, a round-specific value of a latency modification parameter at a time associated with the stimulus-response round; and adjusting, with the processor, the based uncertainty value based on the round-specific value of the latency modification parameter to obtain the uncertainty value for the stimulus-response round.

25. A method according to claim 1 comprising:

performing a calibration operation to determine a base latency estimate, wherein performing the calibration operation comprises:

for a plurality of output calibration iterations:

measuring, with the processor, the output latency of a calibration stimulus signal sent from the processor to the output device via the output data path;

for a plurality of input calibration iterations:

measuring, with the processor, the input latency of a calibration response signal sent from the input device to the processor via the input data path; and determining, with the processor, the base latency estimate to be a sum of a statistical mean of the measured output latencies over the plurality of output calibration iterations and a statistical mean of the measured input latencies over the plurality of input calibration iterations;

determining, with the processor, a latency estimate $L_E$ for each of the plurality of stimulus-response rounds, wherein determining the latency estimate $L_E$ for each stimulus-response round comprises:

ascertaining, with the processor, a round-specific value of a latency modification parameter at a time associated with the stimulus response round; and adjusting, with the processor, the base latency estimate based on the round-specific value of the latency modification parameter to obtain the latency estimate $L_E$ for the stimulus-response round.

26. A method according to claim 1 wherein:

determining, with the processor, the performance indicator comprises evaluating a metric function, the metric function based at least in part on the actual estimated response times $R_{TE}$ over the plurality of stimulus-response rounds;

determining, with the processor, the one or more uncertainty values comprises determining a plurality of uncertainty values, the plurality of uncertainty values comprising an uncertainty value for each stimulus-response round; and determining, with the processor, the confidence value comprises evaluating a metric uncertainty function, the metric uncertainty function based at least in part on the plurality of uncertainty values.

27. A method according to claim 26 wherein the metric function comprises one or more of: a mean response time function for determining a mean of the estimated actual response times $RT_E$ over the plurality of stimulus-response rounds; a standard deviation of response time function for determining a standard deviation of the estimated actual response times $RT_E$ over the plurality of stimulus response rounds; a mean of the fastest ten-percent of response times function for determining a mean of the fastest ten-percent of the estimated actual response times $RT_E$ over the plurality of stimulus-response rounds; mean of the slowest ten-percent of response times function for determining a mean of the slowest ten-percent of the estimated actual response times $RT_E$ over the plurality of stimulus-response rounds; a number of lapses function for counting a number of estimated actual response times $RT_E$ over a lapse threshold over the plurality of stimulus-response rounds; a number of timeouts function for counting a number of estimated actual response times $RT_E$ over a timeout threshold over the plurality of stimulus-response rounds; a mean of the reciprocal response time function for determining a mean of the reciprocal estimated actual response times $RT_E$ over the plurality of stimulus-response rounds; and a standard deviation of the mean reciprocal response time for determining a standard deviation of the mean reciprocal estimated actual response times $RT_E$ over the plurality of stimulus-response rounds.

28. A method according to claim 26 wherein:

determining the performance indicator comprises evaluating a classification function, the classification function based on the evaluated metric function and evaluating the classification function specifying a resulting neurobehavioral performance classification for the stimulus-response test, the resulting neurobehavioral performance classification selected from among a discrete plurality of neurobehavioral performance classifications; and determining, with the processor, the confidence value comprises:

assuming that the metric function is uniformly distributed about a value of the evaluated metric function with boundaries based on one or more distribution-spread functions of the evaluated metric uncertainty function; and determining, with the processor, a probability that the resulting neurobehavioral performance classification is correct by using the assumed uniformly distributed metric function to compute a probability that evaluating the classification function would produce the resulting neurobehavioral performance classification.

29. A method according to claim 28 wherein:

the metric function comprises a mean response time function and the evaluated metric function comprises a mean of the estimated actual response times $RT_E$ over the plurality of stimulus-response rounds;

evaluating the classification function comprises comparing the mean of the estimated actual response times $RT_E$ to a plurality of classification thresholds to thereby specify the resulting neurobehavioral performance classification for the stimulus-response test; and using the assumed uniformly distributed metric function to compute the probability that evaluating the classification function would produce the resulting neurobehavioral performance classification, comprises computing an integral of the assumed uniformly distributed metric function between a pair of classification thresholds corresponding to the resulting neurobehavioral performance classification.

30. A method according to claim 26 wherein:

determining the performance indicator comprises evaluating a classification function, the classification function based on the evaluated metric function and evaluating the classification function specifying a resulting neurobehavioral performance classification for the stimulus-response test, the resulting neurobehavioral performance classification selected from among a discrete plurality of neurobehavioral performance classifications; and determining, with the processor, the confidence value comprises:

assuming that the metric function is normally distributed about a value of the evaluated metric function with a standard deviation based on a distribution-spread function of the evaluated metric uncertainty function; and determining, with the processor, a probability that the resulting neurobehavioral performance classification is correct by using the assumed normally distributed metric function to compute a probability that evaluating the classification function would produce the resulting neurobehavioral performance classification.

31. A method according to claim 30 wherein:
the metric function comprises a mean response time function and the evaluated metric function comprises a mean of the estimated actual response times $RT_E$ over the plurality of stimulus-response rounds;
evaluating the classification function comprises comparing the mean of the estimated actual response times $RT_E$ to a plurality of classification thresholds to thereby specify the resulting neurobehavioral performance classification for the stimulus-response test; and
using the assumed normally distributed metric function to compute the probability that evaluating the classification function would produce the resulting neurobehavioral performance classification, comprises computing an integral of the assumed normally distributed metric function between a pair of classification thresholds corresponding to the resulting neurobehavioral performance classification.

32. A method according to claim 1 wherein determining the performance indicator comprises: determining a mean of the actual estimated response times $R_{TE}$ over the plurality of stimulus-response rounds; and using the mean of the actual estimated response times $R_{TE}$ to select from among a discrete plurality of neurobehavioral performance levels, each of the discrete plurality of neurobehavioral performance levels defined between a corresponding pair of threshold time values.

33. A method according to claim 32 wherein:
determining the one or more uncertainty values comprises determining a plurality of uncertainty values, the plurality of uncertainty values comprising an uncertainty value for each stimulus-response round; and
determining the confidence value comprises determining a probability that the selected neurobehavioral performance level is correct based at least in part on a function of the plurality of uncertainty values.

34. A method according to claim 33 comprising determining a probability that the correct neurobehavioral performance level should have been one of the discrete plurality of neurobehavioral performance levels adjacent to the selected neurobehavioral performance level based at least in part on the function of the plurality of uncertainty values.

35. A method according to claim 1 comprising performing a plurality of calibration operations to determine latency estimates $L_E$, performing each calibration operation comprising:
providing a calibration unit, the calibration unit comprising: a calibration processor, a calibration input device, a calibration output device, a calibration output data path connecting the calibration processor to the calibration output device, and a calibration input data path connecting the calibration input device to the calibration processor;
providing an automatic responder, the automatic responder configured to respond to a calibration stimulus output from the calibration output device by inputting a calibration response at the calibration input device at an automatic response time $T_{RA}$ after the output of the calibration stimulus from the calibration output device;
for a plurality of calibration iterations:
sending a calibration stimulus signal from the calibration processor to the calibration output device via the calibration output data path, the calibration stimulus signal sent from the calibration processor at a first calibration time, the calibration stimulus signal causing the calibration output device to output a calibration stimulus and prompting the automatic responder to respond to the calibration stimulus at the calibration input device;
receiving a calibration response signal from the calibration input device at the calibration processor via the calibration input data path, the calibration response signal received at the calibration processor at a second calibration time;
determining, with the processor, a calibration round-trip signal time $T_{CAL,RTS}$ comprising a time interval between the first and second calibration times;
determining, with the processor, the calibration latency $L_{CAL}$ to be the difference between the calibration round-trip signal time $T_{CAL,RTS}$ and the automatic response time $T_{RA}$;
determining, with the processor, calibration unit latency estimate to be a statistical mean of the calibration latencies $L_{CAL}$ over the plurality of calibration iterations;
recording, with the processor, one or more characterization properties of the calibration unit, the characterization properties comprising at least one of: a calibration unit manufacturer; a calibration unit model; a calibration unit memory size and a calibration unit calibration processor frequency.

36. A method according to claim 35 comprising determining, with the processor, the latency estimate $L_E$, wherein determining the latency estimate $L_E$ comprises:
ascertaining, with the processor, one or more characterization properties of the testing unit, the characterization properties comprising at least one of: a testing unit manufacturer; a testing unit model; a testing unit memory size and a testing unit processor frequency;
comparing, with the processor, the one or more characterization properties of the testing unit to characterization properties of the plurality of calibration units to select a best-matching one of the calibration units; and
determining, with the processor, the latency estimate $L_E$ to be the calibration unit latency estimate corresponding to the best-matching one of the calibration units.

* * * * *